United States Patent
Wang et al.

(10) Patent No.: US 11,994,522 B2
(45) Date of Patent: May 28, 2024

(54) BIOMARKER DETECTION PROCESS AND ASSAY OF NEUROLOGICAL CONDITION

(71) Applicant: Banyan Biomarkers, Inc., Durham, NC (US)

(72) Inventors: Kevin Ka-Wang Wang, Gainesville, FL (US); Ronald L. Hayes, Alachua, FL (US); Uwe R. Mueller, Alachua, FL (US); Zhiqun Zhang, Auburndale, MA (US)

(73) Assignee: BANYAN BIOMARKERS, INC., Durham, NC (US)

( * ) Notice: Subject to any disclaimer, the term of this patent is extended or adjusted under 35 U.S.C. 154(b) by 0 days.

(21) Appl. No.: 16/890,943

(22) Filed: Jun. 2, 2020

(65) Prior Publication Data

US 2021/0011028 A1  Jan. 14, 2021

Related U.S. Application Data

(63) Continuation of application No. 15/709,368, filed on Sep. 19, 2017, now abandoned, which is a continuation of application No. 13/058,748, filed as application No. PCT/US2009/053376 on Aug. 11, 2009, now abandoned.

(60) Provisional application No. 61/271,135, filed on Jul. 18, 2009, provisional application No. 61/218,727, filed on Jun. 19, 2009, provisional application No. 61/097,622, filed on Sep. 17, 2008, provisional application No. 61/188,554, filed on Aug. 11, 2008.

(51) Int. Cl.
*G01N 33/68* (2006.01)
*A61B 5/00* (2006.01)
*G01N 33/577* (2006.01)

(52) U.S. Cl.
CPC ........ *G01N 33/6896* (2013.01); *A61B 5/4064* (2013.01); *G01N 33/577* (2013.01); *G01N 2800/28* (2013.01); *G01N 2800/2871* (2013.01); *G01N 2800/52* (2013.01); *G01N 2800/56* (2013.01); *G01N 2800/60* (2013.01)

(58) Field of Classification Search
CPC ............ G01N 33/6896; G01N 33/577; G01N 2800/28; G01N 2800/2871; G01N 2800/52; G01N 2800/56; G01N 2800/60; A61B 5/4064
See application file for complete search history.

(56) References Cited

U.S. PATENT DOCUMENTS

| | | |
|---|---|---|
| 4,366,241 A | 12/1982 | Tom et al. |
| 4,376,110 A | 3/1983 | David et al. |
| 4,517,288 A | 5/1985 | Geigel et al. |
| 4,702,909 A | 10/1987 | Villarejos et al. |
| 4,837,168 A | 6/1989 | de Jaeger et al. |
| 5,045,694 A | 9/1991 | Beavis et al. |
| 5,118,606 A | 6/1992 | Lynch et al. |
| 5,118,937 A | 6/1992 | Hillenkamp et al. |
| 5,231,000 A | 7/1993 | Majocha et al. |
| 5,234,814 A | 8/1993 | Card et al. |
| 5,252,463 A | 10/1993 | Nelson et al. |
| 5,270,163 A | 12/1993 | Gold et al. |
| 5,475,096 A | 12/1995 | Gold et al. |
| 5,492,812 A | 2/1996 | Vooheis |
| 5,536,639 A | 7/1996 | Siman et al. |
| 5,567,588 A | 10/1996 | Gold et al. |
| 5,595,877 A | 1/1997 | Gold et al. |
| 5,614,649 A | 3/1997 | Iqbal et al. |
| 5,637,459 A | 6/1997 | Burke et al. |
| 5,660,985 A | 8/1997 | Pieken et al. |
| 5,670,637 A | 9/1997 | Gold et al. |
| 5,683,867 A | 11/1997 | Biesecker et al. |
| 5,696,249 A | 12/1997 | Gold et al. |
| 5,707,796 A | 1/1998 | Gold et al. |
| 5,710,132 A | 1/1998 | Moller et al. |
| 5,719,060 A | 2/1998 | Hutchens et al. |
| 5,777,194 A | 7/1998 | Scott et al. |
| 5,792,664 A | 8/1998 | Chait et al. |
| 5,830,870 A | 11/1998 | Iqbal et al. |
| 5,869,336 A | 2/1999 | Mever et al. |
| 5,871,712 A | 2/1999 | Siman |
| 5,990,083 A | 11/1999 | Iqbal et al. |
| 6,011,020 A | 1/2000 | Gold et al. |
| 6,048,703 A | 4/2000 | Siman et al. |
| 6,057,143 A | 5/2000 | Meyer et al. |

(Continued)

FOREIGN PATENT DOCUMENTS

| | | |
|---|---|---|
| EP | 0474765 A1 | 3/1992 |
| EP | 0518955 A1 | 12/1992 |

(Continued)

OTHER PUBLICATIONS

Zhang et al., J of Forensic Medicine, 22(2):88-92, Apr. 2006 (certified translation) (Year: 2006).*
Zee and Go, CT of head trauma, Neuroimaging Clin N Am., Aug.; 8(3): 525-39 (1998); abstract only (Year: 1998).*
Pelinka et al., J Trauma, 57:1006-1012 (2004) (Year: 2004).*
Huh et al., J Neurotrauma (Oct. 2003) 20(10): 975-984 (Year: 2003).*
Meric et al., Journal of Emergency Medicine vol. 38, No. 3, pp. 297-301, Epub May 22, 2008 (Year: 2008).*

(Continued)

*Primary Examiner* — Kimberly Ballard
*Assistant Examiner* — Stacey N MacFarlane
(74) *Attorney, Agent, or Firm* — Oliff PLC

(57) ABSTRACT

The subject invention provides a robust, quantitative, and reproducible process and assay for diagnosis of a neurological condition in a subject. The invention provides measurement of two or more biomarkers in a biological fluid such as CSF or serum resulting in a synergistic mechanism for determining the extent of neurological damage in a subject with an abnormal neurological condition and for discerning subtypes thereof or tissue types subjected to damage.

19 Claims, 23 Drawing Sheets

(56) References Cited

U.S. PATENT DOCUMENTS

| | | |
|---|---|---|
| 6,183,977 B1 | 2/2001 | Doyle et al. |
| 6,225,047 B1 | 5/2001 | Hutchens et al. |
| 6,589,746 B1 | 7/2003 | Zemlan |
| 7,144,708 B2 | 12/2006 | Janigro et al. |
| 7,256,252 B1 | 8/2007 | Siman et al. |
| 7,291,710 B2 | 11/2007 | Hayes et al. |
| 7,396,654 B2 | 7/2008 | Hayes et al. |
| 7,456,027 B2 | 11/2008 | Wang et al. |
| 7,645,584 B2 | 1/2010 | Svetlov et al. |
| 8,048,638 B2 | 11/2011 | Svetlov et al. |
| 8,298,835 B2 | 10/2012 | Wang et al. |
| 8,492,107 B2 | 7/2013 | Wang et al. |
| 8,557,526 B2 | 10/2013 | Ottens et al. |
| 8,642,558 B2 | 2/2014 | Anagli et al. |
| 9,074,019 B2 | 7/2015 | Anagli et al. |
| 9,664,694 B2 | 5/2017 | Wang et al. |
| 9,810,698 B2 | 11/2017 | Wang et al. |
| 10,041,959 B2 | 8/2018 | Wang et al. |
| 10,330,689 B2 | 6/2019 | Wang et al. |
| 10,849,548 B2 * | 12/2020 | McQuiston ...... G01N 33/54366 |
| 10,877,038 B2 * | 12/2020 | McQuiston ............ A61B 6/501 |
| 10,877,048 B2 * | 12/2020 | McQuiston .......... G01N 33/573 |
| 11,016,105 B2 * | 5/2021 | McQuiston ........ G01N 33/6896 |
| 11,022,617 B2 * | 6/2021 | McQuiston ........ G01N 33/6893 |
| 11,078,298 B2 | 8/2021 | Catania et al. |
| 11,221,342 B2 | 1/2022 | Wang et al. |
| 2001/0001285 A1 | 5/2001 | Moh |
| 2002/0123059 A1 | 9/2002 | Ho |
| 2002/0147998 A1 | 10/2002 | McConlogue et al. |
| 2003/0040660 A1 | 2/2003 | Jackowski et al. |
| 2003/0119064 A1 | 6/2003 | Valkirs et al. |
| 2003/0129134 A1 | 7/2003 | Chenard et al. |
| 2003/0199000 A1 | 10/2003 | Valkirs et al. |
| 2004/0121343 A1 | 6/2004 | Buechler et al. |
| 2004/0203083 A1 | 10/2004 | Buechler et al. |
| 2004/0253637 A1 | 12/2004 | Buechler et al. |
| 2005/0063942 A1 | 3/2005 | Clark et al. |
| 2005/0112585 A1 | 5/2005 | Zichi et al. |
| 2005/0130226 A1 | 6/2005 | Ahn |
| 2005/0136489 A1 | 6/2005 | Tseng et al. |
| 2005/0244890 A1 | 11/2005 | Davies |
| 2005/0260654 A1 | 11/2005 | Wang et al. |
| 2005/0260697 A1 | 11/2005 | Wang et al. |
| 2006/0094064 A1 | 5/2006 | Ray et al. |
| 2006/0240480 A1 | 10/2006 | Curdt et al. |
| 2006/0246489 A1 | 11/2006 | Svetlov et al. |
| 2006/0292558 A1 | 12/2006 | O'Neill |
| 2007/0003982 A1 | 1/2007 | Hayes et al. |
| 2007/0027634 A1 | 2/2007 | Mendrick et al. |
| 2007/0042425 A1 | 2/2007 | Hochstrasser et al. |
| 2007/0074972 A1 | 4/2007 | Nassef |
| 2007/0255113 A1 | 11/2007 | Grimes |
| 2007/0298433 A1 | 12/2007 | Sia et al. |
| 2009/0041626 A1 | 2/2009 | Atkin |
| 2009/0068691 A1 | 3/2009 | Dave et al. |
| 2009/0087868 A1 | 4/2009 | Wang et al. |
| 2009/0130658 A1 | 5/2009 | Barlag |
| 2009/0317805 A1 | 12/2009 | Wang et al. |
| 2010/0047817 A1 | 2/2010 | Ottens et al. |
| 2010/0317041 A1 | 12/2010 | Wang et al. |
| 2011/0082203 A1 | 4/2011 | Wang et al. |
| 2011/0097392 A1 | 4/2011 | Wang et al. |
| 2011/0143375 A1 | 6/2011 | Wang et al. |
| 2011/0177974 A1 | 7/2011 | Wang et al. |
| 2012/0028904 A1 | 2/2012 | Anagli et al. |
| 2012/0196307 A1 | 2/2012 | Ottens et al. |
| 2012/0202231 A1 | 8/2012 | Wang et al. |
| 2013/0022982 A1 | 1/2013 | Wang et al. |
| 2013/0029362 A1 | 1/2013 | Jeromin et al. |
| 2013/0029859 A1 | 1/2013 | Svetlov et al. |
| 2014/0018299 A1 | 1/2014 | Mondello et al. |
| 2014/0024053 A1 | 1/2014 | Kobeissy et al. |
| 2014/0178351 A1 | 6/2014 | Svetlov et al. |
| 2014/0228298 A1 | 8/2014 | Anagli et al. |
| 2014/0275294 A1 | 9/2014 | Svetlov et al. |
| 2014/0303041 A1 | 10/2014 | Hayes et al. |
| 2014/0342381 A1 | 11/2014 | Hayes |
| 2015/0141528 A1 | 5/2015 | Larner |
| 2015/0247867 A1 | 9/2015 | Curdt et al. |
| 2015/0259740 A1 | 9/2015 | Pollard et al. |
| 2015/0268252 A1 | 9/2015 | Svetlov et al. |
| 2017/0045534 A1 | 2/2017 | Wang et al. |
| 2017/0146555 A1 | 5/2017 | Wang et al. |
| 2017/0176460 A1 | 6/2017 | Larner |
| 2017/0242036 A1 | 8/2017 | Pollard et al. |
| 2017/0242041 A1 | 8/2017 | Wang et al. |
| 2017/0281738 A1 | 10/2017 | Svetlov et al. |
| 2017/0307640 A1 | 10/2017 | Kobaissy et al. |
| 2018/0031577 A1 | 2/2018 | Wang et al. |
| 2018/0059123 A1 | 3/2018 | Wang et al. |
| 2019/0064187 A1 | 2/2019 | Svetlov et al. |
| 2019/0064188 A1 | 2/2019 | Wang et al. |
| 2020/0003789 A1 | 1/2020 | Wang et al. |
| 2020/0165355 A1 | 5/2020 | Catania et al. |
| 2021/0011028 A1 | 1/2021 | Wang et al. |
| 2021/0347914 A1 | 11/2021 | Catania et al. |
| 2022/0113321 A1 | 4/2022 | Wang et al. |

FOREIGN PATENT DOCUMENTS

| | | |
|---|---|---|
| EP | 0732399 A2 | 9/1996 |
| EP | 0752103 A1 | 1/1997 |
| EP | 0773991 A1 | 5/1997 |
| EP | 0789578 A1 | 8/1997 |
| EP | 0975971 A1 | 2/2000 |
| EP | 1037626 A1 | 9/2000 |
| EP | 1310797 | 5/2003 |
| EP | 1519194 | 3/2005 |
| EP | 2143735 | 1/2010 |
| EP | 2245466 | 11/2010 |
| JP | 2000-505544 | 5/2000 |
| JP | 2003-070498 | 3/2003 |
| JP | 2005-538380 | 12/2005 |
| WO | WO-1990/15331 | 12/1990 |
| WO | WO-1991/013904 | 9/1991 |
| WO | WO-1992/00374 | 1/1992 |
| WO | WO-1993/24834 | 12/1993 |
| WO | WO-1995/026506 | 10/1995 |
| WO | WO-1996/02634 | 2/1996 |
| WO | WO-1996/14857 | 5/1996 |
| WO | WO-1996/34097 | 10/1996 |
| WO | WO-1998/21590 | 5/1998 |
| WO | WO-1999/30707 | 6/1999 |
| WO | WO-1999/51773 | 10/1999 |
| WO | WO-2000/04389 | 1/2000 |
| WO | WO-2000/014546 | 3/2000 |
| WO | WO-2000/56934 | 9/2000 |
| WO | WO-2000/078807 | 12/2000 |
| WO | WO-2002/093174 | 11/2002 |
| WO | WO-2003/016910 | 2/2003 |
| WO | WO-2003/019181 | 3/2003 |
| WO | WO-2003/032894 | 4/2003 |
| WO | WO-2003/062824 | 7/2003 |
| WO | WO-2003/085083 | 10/2003 |
| WO | WO-2004/025298 | 3/2004 |
| WO | WO 2005/113798 A2 * | 4/2004 |
| WO | WO-2004/059293 | 7/2004 |
| WO | WO-2004/078204 | 9/2004 |
| WO | WO-2005/004794 | 1/2005 |
| WO | WO-2005/029087 | 3/2005 |
| WO | WO-2005/029088 | 3/2005 |
| WO | WO-2005/106038 | 11/2005 |
| WO | WO-2005/113798 | 12/2005 |
| WO | WO-2007/007129 | 1/2007 |
| WO | WO-2007/046811 | 4/2007 |
| WO | WO-2007/140188 | 12/2007 |
| WO | WO-2008/008819 | 1/2008 |
| WO | WO-2008/063369 | 5/2008 |
| WO | WO-2008/095136 | 8/2008 |
| WO | WO-2008/097618 | 8/2008 |
| WO | WO-2007/094395 | 7/2009 |
| WO | WO-2009/100131 | 8/2009 |
| WO | WO-2009/129476 | 10/2009 |
| WO | WO-2010/019553 | 2/2010 |

(56) References Cited

FOREIGN PATENT DOCUMENTS

| WO | WO-2010/033912 | 3/2010 |
|---|---|---|
| WO | WO-2010/059242 | 5/2010 |
| WO | WO-2010/148391 | 12/2010 |
| WO | WO-2011/011334 | 1/2011 |
| WO | WO-2011/032155 | 3/2011 |
| WO | WO-2011/123844 | 10/2011 |
| WO | WO-2011/160096 | 12/2011 |
| WO | WO-2012/051519 | 4/2012 |
| WO | WO-2012/141674 | 10/2012 |
| WO | WO-2013/040502 | 3/2013 |
| WO | WO-2014/194329 | 12/2014 |
| WO | WO-2015/157300 | 10/2015 |
| WO | WO-2015/157390 | 12/2016 |
| WO | WO-2018/081649 | 5/2018 |

OTHER PUBLICATIONS

Romner et al., J. Neurotrauma 17 (2000), pp. 641-647 (Year: 2000).*
"Anti-PGP9.5 antibody [13C4/I3C4]ab 8189 11, "Abcam online catalogue, Jan. 1, 1988, Retrieved from the Internet: URL:http://www.abcam.com/PGP95-antibody-13C4-I3C4-ab8189.pdf, retrieved on Jan. 4, 2018, 6 pages.
"Cerebral contusion" published by Wikipedia online on Sep. 13, 2006. Retrieved from http://en.wikipedia.org/wik/Cerebral_contusion. Retrieved on Mar. 20, 2017 1:54:09 PM.
André et al., "NMDA Receptor Alterations in Neurons from Pediatric Cortical Dysplasia Tissue," Cereb Cortex (2004) 14(6):634-646.
Araki et al., "Developmentally regulated expression of Neuro-p24 and its possible function in neurite extension," Neurosci Res (2002) 44(4):379-389.
Aurell et al., "Determination of S-100 and glial fibrillary acidic protein concentrations in cerebrospinal fluid after brain infarction," Stroke (1991) 22(10):1254-1258.
Authoritative Dictionary of IEEE Standard Terms. Seventh Edition. 2000. Excerpt of definitions of "parallel" and "serial".
Baldwin et al., "Intermediate filament change in astrocytes following mild cortical contusion," Glia (1996) 16(3):266-275.
Belay et al., "Creutzfeldt-Jakob Disease in Unusually Young Patients Who Consumed Venison," Arch. Neurol (2001) 58(10):1673-1678.
Berger et al., "Serum Concentrations of Ubiquitin C-Terminal Hydrolase-L1 and αII-Spectrin Breakdown Product 145 kDa Correlate with Outcome after Pediatric TBI," J Neurotrauma (2012) 29(1): 162-167.
Blennow "Cerebrospinal Fluid Protein Biomarkers for Alzheimer's Disease," NeuroRx (2004) 1(2):213-225.
Brief Communication granting Extension of Time for EP 09807153.3, dated Mar. 18, 2019. 4 pages.
Brief Communication Postponing Oral Proceedings for EP 09807153.3, dated Jun. 8, 2020. 2 pages.
Brief Communication re Letter from Proprietor for EP 09807153.3, dated Jan. 9, 2020; 57 pages.
Brief Communication Notification (Proprietor and Opponent) concerning the date of oral proceedings for EP 09807153.3, dated Jun. 8, 2020; 3 pages.
Brief Communication Notifications (Proprietor and Opponent) concerning the date of oral proceedings for EP 09807153.3, dated Aug. 19, 2020; 2 pages.
Brief Communication Notify Proprietor re Written Submissions for EP 09807153.3, dated Apr. 22, 2021; 10 pages.
Brief Communication Notifications (Proprietor and Opponent) concerning the date of oral proceedings for EP 09807153.3, dated Feb. 24, 2021; 6 pages.
Brophy et al., "AlphaII-Spectrin breakdown product cerebrospinal fluid exposure metrics suggest differences in cellular injury mechanisms after severe traumatic brain injury," J Neurotrauma (2009) 26:471-479.
Brophy et al., "Biokinetic Analysis of Ubiquitin C-Terminal Hydrolase-L1 (UCH-L1) in Severe Traumatic Brain Injury Patient Biofluids," J Neurotrauma (2011) 28(6):861-870.
Cao et al., "Cleavage of Bax to p18 Bax accelerates stress-induced apoptosis, and a cathespin-like protease may rapidly degrade p18 Bax," Blood (2003) 102(7):2605-2614.
Casset et al., "A peptide mimetic of an anti-CD4 monoclonal antibody by rational design," Biochem Biophys Res Commun. (2003) 307(1): 198-205.
CDC, Glasgow Coma Scale, published Apr. 19, 2004 [online] Retrieved from https://www.cdc.gov/masstrauma/resources/gcs.pdf; Retrieved on Feb. 7, 2020. (Year: 2004).
Communication of Amended Entries Representative EP 09807153.3, dated Feb. 4, 2019. 1 page.
Communication of Notice of Opposition for EP 09807153.3, dated Nov. 7, 2018,116 pages.
Communication of Notice of Opposition Request for Observations for EP 09807153.3, dated Nov. 16, 2018, 1 page.
Communication Notifications (Proprietor and Opponent) concerning reference File Number for Notice of Appeal proceedings for EP 09807153.3, dated Oct. 12, 2021; 4 pages.
Cookson, "Parkin's substrates and the pathways leading to neuronal damage," Neuromolecular Med (2003) 3(1):1-13.
Cox et al., "Dicyclomine, an M1 Muscarinic Antagonist, Reduces Biomarker Levels, But Not Neuronal Degeneration, in Fluid Percussion Brain Injury," J Neurotrauma (2008) 25(11):1355-1365.
Cutler et al., "Review of the Next Generation of Alzheimer's Disease Therapeutics: Challenges for Drug Development," Prog Neuropsychopharmacol Biol Psychiatry (2001) 25(1):27-57.
Dambinova et al., "Blood Test Detecting Autoantibodies to N-Methyl-D-aspartate Neuroreceptors for Evaluation of Patients with Transient Ischemic Attack and Stroke," Clin Chem (2003) 49(10):1752-1762.
Dambinova et al., "The presence of autoantibodies to N-terminus domain of GluR1 subunit of AMPA receptor in the blood serum of patients with epilepsy," J Neurol Sci (1997) 152(1):93-97.
Dash et al., "Biomarkers for the Diagnosis, Prognosis, and Evaluation of Treatment Efficacy for Traumatic Brain Injury," Neurotherapeutics (2010) 7(1):100-114.
Decision in Opposition Proceeding (Opponent) for EP 09807153.3, dated Jul. 15, 2021; 94 pages.
Decision in Opposition Proceeding (Proprietor) for EP 09807153.3, dated Jul. 15, 2021; 94 pages.
Dekosky et al., "Looking Backward to Move Forward: Early Detection of Neurodegenerative Disorders," Science (2003) 302(5646):830-834.
Del Prete et al., "Migration of dendritic cells across blood and lymphatic endothelial barriers," Thromb Haemost (2006) 95(1):22-28.
Denning et al., "Protein Kinase Cdelta Is Activated by Capase-dependent Proteolysis during Ultraviolet Radiation-induced Apoptosis of Human Keratinocytes," J Biol Chem (1998) 273(45):29995-30002.
Esselman et al., "Review of subject: Classification of the spectrum of mild traumatic brain injury," Brain Injury (1995) 9(4):417-424.
Estrov et al., "Caspase 2 and Caspase 3 Protein Levels as Predictors of Survival in Acute Myelogenous Leukemia," Blood (1998) 92(9):3090-3097.
Everbroeck et al., "A Prospective Study of CSF Markers in 250 Patients with Possible Creutzfeldt-Jakob Disease," J Neurol Neurosurg Psychiatry (2003) 74:1210-1214.
Frijns et al., "Inflammatory Cell Adhesion Molecules in Ischemic Cerebrovascular Disease," Stroke (2002) 33(8):2115-2122.
Hajimohammadreza et al., "A Specific Inhibitor of Calcium/Calmodulin-Dependent Protein Kinase-II Provides Neuroprotection Against NMDA- and Hypoxia/Hypoglycemia-Induced Cell Death," J Neurosci (1995) 15(5):4093-4101.
Hajimohammadreza et al., "Neuronal Nitric Oxide Synthase and Calmodulin-Dependent Protein Kinase II alpha Undergo Neurotoxin-Induced Proteolysis," J Neurochem (1997) 69(3):1006-1013.
Hansen et al., "Frontal cortical synaptophysin in Lewy body diseases: relation to Alzheimer's disease and dementia" J Neurol Neurosurg Psychiatry (1998) 64(5):653-656.

(56) References Cited

OTHER PUBLICATIONS

Hinkle et al., "GFAP and S100β Expression in the Cortex and Hippocampus in Response to Mild Cortical Contusion," J Neurotrama (1997) 14(10):729-738.

Holm et al,, "Functional mapping and single chain construction of the anti-cytokeratin 8 monoclonal antibody TS1," Mol Immunol. (2007) 44(6): 1075-1084.

Inden et al., "Proteasome Inhibitors Protect Against Degeneration of Nigral Dopaminergic Neurons in Hemiparkinsonian Rats," J Pharmacol Sci (2005) 97:203-211.

Information Results from Oral proceedings for EP 09807153.3, dated Jun. 18, 2021; 22 pages.

Jakowec et al., "The native form of alpha-synuclein is not found in the cerebrospinal fluid of patients with Parkinson's disease or normal controls," Neurosci Lett (1998) 253(1):13-16.

Kim et al., "Comparison of Proteome Between Hepatitis B Virus- and Hepatitis C VirusAssociated Hepatocellular Carcinoma," Clin Cancer Res (2003) 9(15):5493-5500.

Kobeissy et al. "Degradation of βII-Spectrin Protein by Calpain-2 and Caspase-3 Under Neurotoxic and Traumatic Brain Injury Conditions," Mol Neurobiol (2015) 52:696-709.

Kobeissy et al. "Novel differential neuroproteomics analysis of traumatic brain injury in rats," Mol Cell Proteomics (2006) 5(10):1887-1898.

Kohler et al., "Continuous Cultures of Fused Cells Secreting Antibody of Predefined Specificity," Nature (1975) 256(5517):495-497.

Koriyama et al., "Proteolytic Activation of Protein Kinase C delta and epsilon by Capase-3 in U937 Cells During Chemotherapeutic Agent-Induced Apoptosis," Cell Signal (1999) 11(11):831-838.

Kronborg et al., "Pre-symptomatic increase in urine-orosomucoid excretion in preeclamptic women," Acta Obstet Gynecol Scand (2007) 86(8):930-937.

Lee et al., "Fit-for-Purpose Method Development and Validation for Successful Biomarker Measurement," Pharm Res (2006) 23(2):312-328.

Lee et al., "Neuroimaging in traumatic brain imaging," NeuroRx (2005) 2(2):372-383.

Letter Requesting Interpreter of Oral Proceedings for EP 09807153. 3, dated Apr. 22, 2020, 3 pages.

Letter Requesting Interpreter of Oral Proceedings for EP 09807153. 3, dated Apr. 16, 2021, 4 pages.

Letter Requesting Postponement of Oral Proceedings for EP 09807153. 3, dated Apr. 2, 2020, 4 pages.

Letter Reply to date proposed for Oral proceedings for EP 09807153. 3, dated Aug. 6, 2020, 4 pages.

Letter Reply to date proposed for Oral proceedings for EP 09807153. 3, dated Aug. 7, 2020, 3 pages.

Letter Regarding Additional Attendess for Oral proceedings for EP 09807153.3, dated Jun. 7, 2021; 3 pages.

Letter Regarding Transfer of Representation of Opponent for Oral proceedings for EP 09807153.3, dated Jun. 7, 2021; 4 pages.

Letter Regarding Notice of Appeal of Opponent for Oral proceedings for EP 09807153.3, dated Jun. 7, 2021; 5 pages.

Lewis et al., "Alpha-II spectrin breakdown products in aneurysmal subarachnoid hemorrhage: a novel biomarker of proteolytic injury," J Neurosurg (2007) 107(4):792-796.

Lewis et al., "Utility of Serum Biomarkers in the Diagnosis and Stratification of Mild Traumatic Brain Injury," Acad Emerg Med. (2017) 24(6):710-720.

Li et al., "Expression of the ubiquitin carboxyl-terminal hydrolase PGP 9.5 in axons following spinal cord compression trauma. An immunohistochemical study in the rat," APMIS (1997) 105(5):384-390.

Liu et al., "The UCH-L1 Gene Encodes Two Opposing Enzymatic Activities that Affect α-Synuclein Degradation and Parkinson's Disease Susceptibility," Cell (2002) 111(2):209-218.

Liu et al., "Ubiquitin C-terminal hydrolase-L1 as a biomarker for ischemic and traumatic brain injury in rats," Eur J Neurosci (2010) 31(4):722-732.

Lowe et al., "Ubiquitin carboxyl-terminal hydrolase (PGP 9.5) is selectively present in ubiquitinated inclusion bodies characteristic of human neurodegenerative diseases," J Pathol (1990) 161(2):153-160.

MacCallum et al., "Antibody-antigen interactions: contact analysis and binding site topography," J Mol Biol (1996) 262(5):732-745.

Mao et al., "The value of serum myelin basic protein in assessment of severity of acute closed head trauma," Hua Xi Yi Ke Da Xue Bao (1995) 26(2):135-137 (Abstract).

Martinez et al., Granulomatous Amebic Encephalitis in a Patient with AIDS: Isolation of *Acanthamoeba* sp. Group II from Brain Tissue and Successful Treatment with Sulfadiazine and Fluconazole, J Clin Microbiol (2000) 38(10):3892-3895.

Matevossian et al., "Neuronal Nuclei Isolation from Human Postmortem Brain Tissue," J Vis Exp (2008) 20:pii 914.

Maynard et al., "Excess placental soluble fms-like tyrosine kinase 1 (sFlt1) may contribute to endothelial dysfunction, hypertension, and proteinuria in preeclampsia," J Clin Invest (2003) 111(5): 649-658.

McGinnis et al., "Calcium/Calmodulin-dependent Protein Kinase IV Is Cleaved by Caspase-3 and Calpain in SH-SY5Y Human Neuroblastoma Cells Undergoing Apoptosis," J Biol Chem (1998) 273(32):19993-20000.

Miller et al., "Excitatory amino acid receptor subtype binding following traumatic brain injury" Brain Res (1990) 526(1):103-107.

Missler et al., "Measurement of Glial Fibrillary Acidic Protein in Human Blood: Analytical Method and Preliminary Clinical Results," Clin Chem (1999) 45(1):138-141.

Miura et al., "An Enzymatic Method for the Assay of Serum Argininosuccinate Lyase," Anal Biochem (1987) 164(2):482-487.

Mondello et al., "Clinical Utility of Serum Levels of Ubiquitin C-Terminal Hydrolase as a Biomarker for Severe Traumatic Brain Injury," Neurosurgery (2012) 70(3):666-675.

Mondello et al., "Neuronal and glial markers are differently associated with computed tomography findings and outcome in patients with severe traumatic brain injury: a case control study," Crit Care (2011) 15(3):R156.

Mondello et al., "αII-Spectrin Breakdown Products (SBDPs): Diagnosis and Outcome in Severe Traumatic Brain Injury Patients," J Neurotrauma (2010) 27(7):1203-1213.

Mukerjee et al., "Caspase-Mediated Calcineurin Activation Contributes to IL-2 Release during T Cell Activation," Biochem Biophys Res Commun (2001,) 285(5):1192-1199.

N.N.: "Catalogue# MCA-BH7: Mouse Monoclonal Antibody to Ubiquitin C-Terminal Hydrolase 1," Online catalogue of EnCor Biotechnology, Jun. 23, 2014, Retrieved from the Internet: URL:http://encorbio.com/Datasheet/MCA-BH7Product Data Sheet.pdf, retrieved on Jan. 27, 2018, 2 pages.

Nath et al., "Non-erythroid α-spectrin breakdown by calpain and interleukin 1β-converting-enzyme-like protease(s) in apoptotic cells: contributory roles of both proteasefamilies in neuronal apoptosis," Biochem J (1996) 319(Pt 3):683-690.

Nawashiro et al., "Selective vulnerability of hippocampal CA3 neurons to hypoxia after mild concussion in the rat," Neurol Res (1995) 17(6):455-460.

Nylen et al., "Increased serum-GFAP in patients with severe traumatic brain injury is related to outcome," J Neurol Sci (2006) 240(1-2):85-91.

Ohta et al., "Clinical and Analytical Evaluation of an Enzyme Immunoassay for Myelin Basic Protein in Cerebrospinal Fluid," Clin Chem (2000)46(9):1326-1330.

Ontario Neurotrauma Foundation, Guideline for Concussion/Mild Traumatic Brain Injury & Persistent Symptoms, May 2018. (Year: 2018).

Papa et al., "Biomarkers improve clinical outcome predictors of mortality following non-penetrating severe traumatic brain injury," Neurocrit Care (2015) 22(1):52-64.

Papa et al., "Elevated Levels of Serum Glial Fibrillary Acidic Protein Breakdown Products in Mild and Moderate Traumatic Brain Injury are Associated With Intracranial Lesions and Neurosurgical Intervention," Ann Emerg Med (2011) 59(6):471-483.

Papa et al., "GFAP Out-Performs S100β in Detecting Traumatic Intracranial Lesions on Computed Tomography in Trauma Patients

(56) References Cited

OTHER PUBLICATIONS with Mild Traumatic Brain Injury and Those with Extracranial Lesions," J Neurotrauma (2014) 31(22):1815-1822.
Papa et al., "Serum levels of ubiquitin C-terminal hydrolase distinguish mild traumatic brain injury from trauma controls and are elevated in mild and moderate traumatic brain injury patients with intracranial lesions and neurosurgical intervention," J Trauma Acute Care Surg (2012) 72(5):1335-1344.
Papa et al., "Time Course and Diagnostic Accuracy of Glial and Neuronal Blood Biomarkers GFAP and UCH-L1 in a Large Cohort of Trauma Patients With and Without Mild Traumatic Brain Injury," JAMA Neurol (2016) 73(5):551-560.
Papa et al., "Use of biomarkers for diagnosis and management of traumatic brain injury patients," Expert Opin Med Diagn (2008) 2(8):937-945.
Papa, L. et al. "Ubiquitin C-terminal hydrolase is a novel biomarker in humans for severe traumatic brain injury," Crit Care Med (2010) 38(1):138-144.
Pearl et al., "Clinical Aspects of the Disorders of GABA Metabolism in Children," Curr Opin Neurol (2004) 17(2):107-113.
Pekny et al., "The Role of Astrocytes and Complement System in Neural Plasticity," Int Rev Neurobiol (2007) 82:95-111.
Pelinka et al., "GFAP Versus S100B in Serum After Traumatic Brain Injury: Relationship to Brain Damage and Outcome," J Neurotrama (2004) 21(11):1553-1561.
Pelinka et al., "Glial Fibrillary Acidic Protein in Serum After Traumatic Brain Injury and Multiple Trauma," J Trauma (2004) 57(5):1006-1012.
Petricoin et al., "Clinical proteomics: translating benchside promise into bedside reality," Nat Rev Drug Discov (2002) 1(9):683-695.
Petzold et al., "An ELISA for glial fibrillary acidic protein." J Immunol Methods (2004) 287(1-2):169-177.
Petzold et al., "Role of Serum S100B as an Early Predictor of High Intracranial Pressure and Mortality in Brain Injury: A Pilot Study," Crit Care Med. (2002) 30(12), 2705-2710.
Pike et al., "Accumulation of non-erythroid alpha II-spectrin and calpain-cleaved alpha II-spectrin breakdown products in cerebrospinal fluid after traumatic brain injury in rats," J Neurochem (2001) 78(6):1297-1306.
Pike et. al., "Temporal relationships between de novo protein synthesis, calpain and caspase 3-like protease activation, and DNA fragmentation during apoptosis," J. Neurosci Res (1998) 52(5):505-520.
Pineda et al., "Clinical significance of alphaII-spectrin breakdown products in cerebrospinal fluid after severe traumatic brain injury," J Neurotrauma (2007) 24(2)354-366.
Poletaev et al., "Serum anti-S100b, anti-GFAP and anti-NGF autoantibodies of IgG class in healthy persons and patients with mental and neurological disorders," Autoimmunity (2000) 32(1):33-38.
Posmantur et al. "A calpain inhibitor attenuates cortical cytoskeletal protein loss after experimental traumatic brain injury in the rat," Neuroscience (1997) 77(3):875-888.
Raabe et al., "Serum markers of brain damage and outcome prediction in patients after severe head injury," Br J Neurosurg (1999) 56-59.
Request Extension of Time for EP 09807153.3, dated Mar. 11, 2019, 3 pgs.
Response to Opposition for EP 09807153.3, dated May 24, 2019; 75 pages.
Ringger et al., "A novel marker for traumatic brain injury: CSF alphaII-spectrin breakdown product levels," J Neurotrauma (2004) 21(10):1443-1456.
Rosengren, L. et al. "Patients with Amyotrophic Lateral Sclerosis and Other Neurodegenerative Diseases Have Increased Levels of Neurofilament Protein in CSF", Journal of Neurochemistry, 1996, pp. 2013-2018, vol. 67, No. 5.
Rudikoff et al., "Single amino acid substitution altering antigen-binding specificity," Proc Natl Acad Sci U S A. (1982) 79(6):1979-1983.

Saido et al., "Spatial Resolution of Fodrin Proteolysis in Postischemic Brain," J Biol Chem (1993) 268(33):25239-25243.
Sanchez et al., "Cystatin C as a Potential Cerebrospinal Fluid Marker for the Diagnosis of Creutzfeldt-Jakob Disease," Proteomics (2004) 4(8):2229-2233.
Sankiewicz et al., "Development of surface plasmon resonance imaging biosensors for detection of ubiquitin carboxyl-terminal hydrolase L1," Anal Biochem (2015) 469:4-11.
Schwab et al., "Cleavage of plasma membrane calcium pumps by caspases: a link between apoptosis and necrosis," Cell Death Differ (2002) 9(8):818-831.
Shea, T. et al. "Calcium Influx into Human Neuroblastoma Cells Induces ALZ-50 Immunoreactivity: Involvement of Calpain-Mediated Hydrolysis of Protein Kinase C", Journal of Neurochemistry, 1996, pp. 1539-1549, vol. 66, No. 4.
Shigeta, K. et al. "Fragmentation of a 70000-dalton calpastatin molecule upon its complex formation with calpain", Biochem. Int., 1984, pp. 327-333, vol. 9, No. 3. Abstract only.
Siman et al., "Biomarker evidence for mild central nervous system injury after surgically-induced circulation arrest," Brain Research, 1213:1-11, Jun. 5, 2008.
Sjögren et al., "Neurofilament Protein in Cerebrospinal Fluid: A Marker of White Matter Changes," J Neurosci Res (2001) 66(3):510-516.
Smith et al., "Protein Accumulation in Traumatic Brain Injury," NeuroMolecular Med (2003) 4(1-2):59-72.
Spinal Cord Injury Journal, Contusion vs. Concussion: Understanding the Difference by Zawn Villines. Pulbished online Nov. 23, 2015. Retrieved from <https://web-beta.archive.org/web/20151202013742/http://www.spinalcord.com/blog/contusion-vs.-concussion-understanding-the-difference>. Retrieved on May 4, 2017 12:31:00 PM.
Statement for Grounds of Appeal for EP 09807153.3, dated Nov. 24, 2021; 39 pages.
Su et al., "Levels of the potential biomarker p11 in peripheral blood cells distinguishes patients with PTSD from those with other major psychiatric disorders," J Psychiatr Res. (2009);43(13):1078-85.
Summons to Attend Oral Proceedings for EP 09807153.3, dated Oct. 17, 2019, 18 pgs.
Summons to Attend Oral Proceedings—OPPO for EP 09807153.3, dated Jul. 6, 2020, 14 pgs.
Summons to Attend Oral Proceedings for EP 09807153.3, dated Jul. 6, 2020, 14 pgs.
Summons to Attend Oral Proceedings—OPPO for EP 09807153.3, dated Jan. 1, 2021; 22 pgs.
Summons to Attend Oral Proceedings for EP 09807153.3, dated Jan. 1, 2021; 22 pgs.
Tabuchi et al., "Regulation of Genes for Inducible Nitric Oxide Synthase and Urea Cycle Enzymes in Rat Liver in Endotoxin Shock," Biochem Biophys Res Commun (2000) 268(1):221-224.
Taheri et al. "The Role of Hypocretins (Orexins) in Sleep Regulation and Narcolepsy," Annu Rev Neurosci (2002) 25:283-313.
Teunissen et al., "Biochemical Markers Related to Alzheimer's Dementia in Serum and Cerebrospinal Fluid," Neurobiol Aging (2002) 23(4):485-508.
Tooney et al., "Neurons Expressing Calcium-binding Proteins in the Prefrontal Cortex in Schizophrenia", Prog Neuropsychopharmacol Biol Psychiatry (2004) 28(2):273-278.
Toth et al., "Lateral Ventricle Volume Asymmetry Predicts Midline Shift in Severe Traumatic Brain Injury," J Neurotrauma (2015) 32(17):1307-1311.
Towern et al., "Detection of neuron-specific protein gene product (PGP) 9.5 in the rat and zebrafish using anti-human PGP9.5 antibodies," Neurosci Lett (1996) 210(1)21-24.
Toyota et al., "Calpain-induced Bax-cleavage product is a more potent inducer of cell death than wild-type Bax," Cancer Lett (2003) 189(2):221-230.
U.S. Appl. No. 15/802,489, filed Nov. 3, 2017, by Wang et al.
Urrea et. al., "Widespread cellular proliferation and focal neurogenesis after traumatic brain injury in the rat," Restor Neurol and Neurosci (2007) 25(1):65-76.

(56) References Cited

OTHER PUBLICATIONS

Van Geel et al., "Measurement of glial fibrillary acidic protein in blood: an analytical method," Clin Chim Acta (2002) 326(1-2):151-154.
Van Voorhis et al., "Understanding Power and Rules of Thumb for Determining Sample Sizes," Tutorials I Quantitative Methods for Psychology (2007) 3(2):43-50.
Vercauteren, "Proteomic approaches in brain research and neuropharmacology," European Journal of Pharmacology, Oct. 1, 2004, vol. 500, No. 1-3, p. 385-398, Elsevier Science, NL.
Villines, "Contusion vs. Concussion: Understanding the Difference," Published on Nov. 23, 2015. Retrieved from https://www.spinalcord.com/blog/contusion-vs.-concussion-understanding-the-difference and retrieved on Jan. 3, 2018.
Vos et al., "Glial and neuronal proteins in serum predict outcome after severe traumatic brain injury," Neurology (2004) 62(8):1303-1310.
Vos et al., "Increased GFAP and S100β but not NSE serum levels after subarachnoid haemorrhage are associated with clinical severity" Eur J Neurol (2006) 13(6):632-638.
Wang et al., "A study of HSP70 and NF in brain contusion timing," Fa Yi Xue Za Zhi (2000) 16(3):132-134 (Abstract).
Ward et al., "Binding Activities of a Repertoire of Single Immunoglobulin Variable Domains Secreted from *Escherichia coli*," Nature (1989) 341(6242):544-546.
Wilson et al., "Functional Genomics and Proteomics: Application in Neurosciences," J Neurol Neurosurg Psychiatry (2004) 75(4):529-538.
Wilson et al., "The Structure of an Antigenic Determinant in a Protein," Cell. (1984) 37:767-778.
Woertgen et al., "Glial and neuronal serum markers after controlled cortical impact injury in the rat," Acta Neurochir Suppl. (2002) 81:205-7.
Written Submissions for EP 09807153.3, dated Apr. 24, 2020, 15 pgs.
Written Submissions for EP 09807153.3, dated Dec. 31, 2019, 60 pgs.
Written Submissions for EP 09807153.3, dated Apr. 16, 2021, 11 pgs.
Xu et. al., "Facilitated Sprouting in a Peripheral Nerve Injury," Neuroscience (2008) 152(4):877-887.
Yamauchi et al., "Ubiquitin-Mediated Stress Response in the Spinal Cord After Transient Ischemia," Stroke (2008) 39(6):1883-1889.
Yohrling et al., "Inhibition of Tryptophan Hydroxylase Activity and Decreased 5-HT1A Receptor Binding in a Mouse Model of Huntington's Disease," J Neurochem (2002) 82(6):1416-1423.
Yu et al., "Accumulation of immunoreactivity to ubiquitin carboxyl-terminal hydrolase PGP 9.5 in axons of human cases with spinal cord lesions," APMIS (1998) 106(11):1081-1087.
Zaffaroni "Biological Indicators of the Neurodegenerative Phase of Multiple Sclerosis", Neurol Sci (2003) 24:S279-S282.
Zemlan et al., "Quantification of axonal damage in traumatic brain injury: affinity purification and characterization of cerebrospinal fluid tau proteins," J Neurochem (1999) 72(2):741-750.
Zhang et al., "Phenotypes of T Cells Infiltrating the Eyes in Autoimmune Anterior Uveitis Associated with EAE," Invest Ophthalmol Vis Sci (2002) 43(5):1499-150818.
"Recommendations of the German Society for Clinical Chemistry," Z. klin. Chem. u. klin. Biochem., 1972, pp. 182-192.
Adams et al., "The neuropathology of the vegetative state after an acute brain insult," Brain (2000) 123:1327-1338.
Ankeny et al., "Mechanisms and implications of adaptive immune responses after traumatic spinal cord injury," Neuroscience (2009) 158:1112-1121; Epub Jul. 4, 2008.
Arnaud et al., "Proteasome-caspase-cathepsin sequence leading to tau pathology induced by prostaglandin J2 in neuronal cells," J Neurochem (2009) 110(1):328-342.

Bartus et al., "Time-related neuronal changes following middle cerebral artery occlusion: implications for therapeutic intervention and the role of calpain," J Cereb Blood Flow Metab (1995) 15(6):969-979.
Bauman et al., "An introductory characterization of a combat-casualty-care relevant swine model of closed head injury resulting from exposure to explosive blast*," Journal of Neurotrauma (2009) 26:841-860.
Beer et al., "Temporal Profile and Cell Subtype Distribution of Activated Caspase-3 Following Experimental Traumatic Brain Injury," J Neurochem (2000) 75:1264-1273.
Binder et al., "The Distribution of Tau in the Mammalian Central Nervous System," J Cell Biol (1985)101:1371-1378.
Bitsch et al., "Serum Tau Protein Level as a Marker of Axonal Damage in Acute Ischemic Stroke," Eur Neurol (2002) 47(1):45-51.
Borghi et al., "Full length alpha-synuclein is present in cerebrospinal fluid from Parkinson's disease and normal subjects," Neurosci Lett (2000) 287(1):65-67.
Bornstein et al., "Antibodies to brain antigens following stroke," Neurology (2001) 56(4):529-530.
Bramlett et al., "Quantitative structural changes in white and gray matter 1 year following traumatic brain injury in rats," Acta Neuropathologica (2002) 103:607-614.
Buki et al., "Cytochrome c Release and Caspase Activation in Traumatic Axonal Injury," J Neurosci (2000) 20(8):2825-2834.
Canu et al., "Tau Cleavage and Dephosphorylation in Cerebellar Granule Neurons Undergoing Apoptosis," J Neurosci (1998) 18(18):7061-7074.
Chekhonin et al., "Enzyme immunoassay of antibodies to neurospecific proteins in examination of blood-brain barrier function," Immunologiya (1996) 0(2):67-69.
Christman et al., "Ultrastructural Studies of Diffuse Axonal Injury in Humans." J Neurotrauma (2009) 11:173-186.
Chung et al., "Proapoptotic Effects of Tau Cleavage Product Generated by Caspase-3," Neurobiol Dis (2001) 8(1):162-172.
Clark et al., "Caspase-3 Mediated Neuronal Death After Traumatic Brain Injury in Rats," J Neurochem (2000) 74(2):740-753.
Cotman et al., "The Role of Caspase Cleavage of Tau in Alzheimer Disease Neuropathology," J Neuropathol Exp Neurol (2005) 64(2):104-112.
De Kruijk et al., "S-100B and neuron-specific enolase in serum of mild traumatic brain injury patients," Acta Neurol. Scand. (2001) 103:175-179.
Delobel et al., "Proteasome inhibition and Tau proteolysis: an unexpected regulation," FEBS Lett (2005) 579(1):1-5.
Dixon et al., "A controlled cortical impact model of traumatic brain injury in the rat," J Neurosci Methods (1991) 39(3):253-262.
Drubin et al., "Tau Protein Function in Living Cells," J Cell Biol (1986) 103(6):2739-2746.
Dvorak et al., "Characterisation of the diagnostic window of serum glial fibrillary acidic protein for the differentiation of intracerebral haemorrhage and ischaemic stroke," Cerebrovasc Dis (2009) 27:37-41.
ECG Guidelines, "Part 7: The Era of Reperfusion, Section 2: Acute Stroke", Circulation 2000;102(suppl 1):1-204-1-216, https://doi.org/10.1161/01.CIR.102.suppl_ 1.1-204 (Year: 2000).
Eikelenboom et al., "Multiple sclerosis, Neurofilament light chain antibodies are correlated to cerebral atrophy," Neurology (2003) 60(2):219-223.
El-Fawal et al., "Autoantibodies to neurotypic and gliotypic proteins as biomarkers of neurotoxicity: assessment of trimethyltin (TMT)," Neurotoxicology (2008) 29(1):109-115.
Finfer et al., "A comparison of albumin and saline for fluid resuscitation in the intensive care unit," N Engl J Med (2004) 350(22):2247-2256.
Foerch et al., "Serum glial fibrillary acidic protein as a biomarker for intracerebral hemorrhage in patients with acute stroke," J Neurol Neurosurg Psychiatry (2006) 77:181-184.
Franz et al., "Amyloid beta 1-42 and tau in cerebrospinal fluid after severe traumatic brain injury," Neurology (2003) 60(9):1457-1461.
Gabbita et al., "Cleaved-Tau: A Biomarker of Neuronal Damage after Traumatic Brain Injury," J Neurotrauma (2005) 22(1):83-94.

(56) References Cited

OTHER PUBLICATIONS

Gamblin et al., "Caspase cleavage of tau: Linking amyloid and neurofibrillary tangles in Alzheimer's disease," Proc Natl Acad Sci USA (2003) 100(17):10032-10037.

Garcia et al., "Going new places using an old MAP: tau, microtubules and human neurodegenerative disease" Curr Opin Cell Biol (2001) 13(1):41-48.

Garcia-Sierra et al., "Truncation of Tau Protein and its Pathological Significance in Alzheimer's Disease," J Alzheimers Dis (2008) 14(4):401-409.

Gaskin et al., "Patients with clinically diagnosed senile dementia of the Alzheimer type make autoantibodies that react with neurofibrillary tangles," Clinical Research (1986) 34(2): 669A.

Giza et al., "The Neurometabolic Cascade of Concussion," J Athl Train (2001) 36(3):228-235.

Goryunova et al., "Glutamate Receptor Autoantibody Concentrations in Children with Chronic Post-Traumatic Headache," Neuroscience and Behavioral Physiology (2007) 37(8):761-764.

Gruden et al., "Differential neuroimmune markers to the onset of Alzheimer's disease neurodegeneration and dementia: autoantibodies to Abeta((25-35)) oligomers, S100b and neurotransmitters," J Neuroimmunol (2007) 186(1-2):181-192.

Grus et al., "Analysis of complex autoantibody repertoires by surface-enhanced laser desorption/ionization-time of flight mass spectrometry," Proteomics (2003) 3(6):957-961.

Guillozet-Bongaarts et al., "Tau truncation during neurofibrillary tangle evolution in Alzheimer's disease," Neurobiol Aging (2005) 26(7):1015-1022.

Hailer., "Immunosuppression after traumatic or ischemic CNS damage: It is neuroprotective and illuminates the role of microglial cells," Progres Neurobiol. (2008) 84:211-233.

Hamaoui et al., "Real-Time Quantitative PCR Measurement of Circulatory Rhodopsin mRNA in Healthy Subjects and Patients with Diabetic Retinopathy," Annals of the New York Academy of Sciences (2004) 1022:152-156.

Hasselmann et. al., "Extracellular Tyrosinase mRNA within Apoptotic Bodies is Protected from Degradations in Human Serum," Clinical Chemistry (2001) 47(8):1488-1489.

Hayakawa, T. et al., "Astroprotein (GFAP) Levels in Cerebrospinal Fluid of Stroke Patients," Neurol Med Chir (Tokyo)24, 13-18, 1984.

Herrmann et al., "Release of Glial Tissue-Specific Proteins After Acute Stroke: A comparative analysis of serum concentrations of protein S-100B and glial fibrillary acidic protein," Stroke (2000) 31(11):2670-2677.

Hesselink, "Imaging of Stroke and Cerebral Ischemia", Aug. 2003, 9 pages, retrieved from https://web.archive.org/web/20030826111030/ http://spinwarp.ucsd.edu/neuroweb/Text/br-71 0.htm on May 6, 2018 (Year: 2003).

Higuchi et al., "Tau and axonopathy in neurodegenerative disorders," Neuromolecular Med (2002) 2(2):131-150.

Honda et al., "Serum glial fibrillary acidic protein is a highly specific biomarker for traumatic brain injury in humans compared with S-100B and neuron-specific enolase," J. Trauma (2010) 69:104-109.

Hozumi et al., "GFAP mRNA levels following stab wounds in rat brain," Brain Res (1990) 534(1-2):291-294.

Ingebrigsten et al., "Biochemical serum markers for brain damage: A short review with emphasis on clinical utility in mild head injury," Restorative Neurology and Neuroscience (2003) 21(3):171-176.

Johnson et al., "Proteolysis of Tau by Calpain," Biochem Biophys Res Commun (1989) 163(3):1505-1511.

Kadota et al., "A Newly Identified Membrane Protein Localized Exclusively in Intracellular Organelles of Neurons," Mol Brain Res (1997) 46(1-2):265-273.

Kampfl et al., "Mechanisms of Calpain Proteolysis Following Traumatic Brain Injury: Implications for Pathology and Therapy: A Review and Update," J Neurotrauma (1997) 14(3):121-134.

Kiraly et al., "Traumatic Brain Injury and Delayed Sequelae: A Review—Traumatic Brain Injury and Mild Traumatic Brain Injury (Concussion) are Precursors to Later-Onset Brain Disorders, Including Early-Onset Dementia," Scientific World Journal (2007) 12(7):1768-1776.

Knoblach et al., "Multiple Caspases Are Activated after Traumatic Brain Injury: Evidence for Involvement in Functional Outcome," J Neurotrama (2002) 19(10):1155-1170.

Kosik et al., "MAP2 and Tau Segregate into Dendritic and Axonal Domains After the Elaboration of Morphologically Distinct Neurites: An Immunocytochemical Study of Cultured Rat Cerebrum," J Neurosci (1987) 7(10):3142-3153.

Kovesdi et al., "Update on protein biomarkers in traumatic brain injury with emphasis on clinical use in adults and pediatrics", Acta Neurochirurgica (2010) 152(1):1-17.

Krishnamurthy et al., "Molecular and biologic markers of premalignant lesions of human breast," Adv Anat Pathol (2002) 9(3):185-197.

Lamers et al., "Protein S-100b, Neuron-Specific Enolase (NSE), Myelin Basic Protein (MBP) and Glial Fibrillary Acidic Protein (GFAP) in Cerebrospinal Fluid (CSF) and Blood of Neurological Patients," Brain Res Bull (2003) 61(3): 261-264.

Le Prince et al., "Alterations of glial fibrillary acidic protein mRNA level in the aging brain and in senile dementia of the Alzheimer type," Neurosci Lett (1993) 151(1):71-73.

Lee et al., "Rapid increase in immunoreactivitiy to GFAP in astrocytes in vitro induced by acidic pH is mediated by calcium influx and calpain I," Brain Research (2000) 864(2): 220-229.

Leon et al., "Free DNA in the Serum of Cancer Patients and the Effect of Therapy," Patients Cancer Research (1977) 37:646-650.

Li et al., "Peptide alpha-Keto Ester, alpha-Keto Amide, and alpha-Keto Acid Inhibitors of Calpains and Other Cysteine Proteases," J Med Chem (1993) 36(22):3472-3480.

Litersky et al., "Phophorylation, calpain proteolysis and tubulin binding of recombinant human tau isoforms," Brain Res (1993) 604:32-40.

Lo et al., "Pediatric brain trauma outcome prediction using paired serum levels of inflammatory mediators and brain-specific proteins," Journal of Neurotrauma (2009) 26:1479-1487.

Lo et. al., "Presence of fetal DNA in maternal plasma and serum," The Lancet (1997) 350:485-487.

Lumpkins et al., "Glial Fibrillary Acidic Protein is Highly Correlated With Brain Injury," J Trauma (2008) 65(4):778-782.

Mao et al., "Electrochemiluminescence assay for basic carboxypeptidases: inhibition of basic carboxypeptidases and activation of thrombin-activatable fibrinolysis inhibitor," Anal Biochem (2003) 319(1):159-170.

McComb et al., "Alkaline Phosphatase," 1979, Plenum Press, New York, D Bibliography pages only.

McCraken et al., "Calpain activation and cytoskeletal protein breakdown in the corpus callosum of head-injured patients," J Neurotrauma (1999) 16(9):749-761.

McGinnis et al., "Alterations of Extracellular Calcium Elicit Selective Modes of Cell Death and Protease Activation in SH-SY5Y Human Neuroblastoma Cells," J Neurochem (1999) 72(5):1853-1863.

McKee et al., "Chronic traumatic encephalopathy in athletes: progressive tauopathy following repetitive head injury," J Neuropathol Exp Neurol (2009) 68(7):709-735.

McKnight et al., "Serum antibodies in epilepsy and seizure-associated disorders," Neurology (2005) 65(11):1730-1736.

McLendon et al., "Immunohistochemistry of the glial fibrillary acidic protein: basic and applied considerations," Brain Pathol (1994) 4(3):221-228.

Medana et al., "Axonal damage: a key predictor of outcome in human CNS diseases," Brain (2003) 126(3):515-530.

Menke et al., "Improved Conditions for Isolation and Quantification of RNA in Urine Specimens," Annals of the New York Academy of Sciences (2004) 1022:185-189.

Miller et al., "Utilizing clinical factors to reduce head CT scan ordering for minor head trauma patients," J. Emerg. Med. (1997) 15(4):453-457.

Mohideen, "Brain natriuretic peptide is more than a marker," Ceylon Medical Journal, Sep. 2002 47(3):81-82.

(56) References Cited

OTHER PUBLICATIONS

Moniem et al., "Autoantibodies to neurofilaments (NF), glial fibrillary acidic protein (GFAP) and myelin basic protein (MBP) in workers exposed to lead," J. Egyptian Public Health Assoc (1999) 74 (1-2): 121-138.

Morozov et al., "Autoantibodies against nerve tissue proteins long after cranio-cerebral injury," Vopr Med Khim (1996) 42(2):147-152.

Mouser et al., "Caspase-Mediated Cleavage of Glial Fibrillary Acidic Protein within Degenerating Astrocytes of the Alzheimer's Disease Brain," Am J Pathol (2003 168(3):936-946.

Muller et al., "Methylated DNA as a possible screening marker for neoplastic disease in several body fluids," Expert Review of Molecular Diagnostics (2003) 3(4):443-458.

Nakanishi et al., "Molecular Characterization of a Transport Vesicle Protein Neurensin-2, a homologue of Neurensin-1, expressed in neural cells," Brain Res (2006) 1081(1):1-8.

Nath et al., "Activation of apoptosis-linked caspase(s) in NMDA-injured brains in neonatal rats," Neurochem Int (2000) 36(2):119-126.

Nath et al., "Development and characterization of antibodies specific to caspase-3-produced alpha II-spectrin 120 kDa breakdown product: marker for neuronal apoptosis," Neurochem Int (2000) 37(4):351-361.

Nath et al., "Effects of ICE-like protease and calpain inhibitors on neuronal apoptosis," Neuroreport (1996) 8(1):249-255.

Nath et al., "Evidence for Activation of Caspase-3-Like Protease in Excitotoxin- and Hypoxia/Hypoglycemia-Injured Neurons," J Neurochem (1998) 71:186-195.

Newcomb et al., "Immunohistochemical study of calpain-mediated breakdown products to alpha-spectrin following controlled cortical impact injury in the rat," J Neurotrauma (1997) 14(6):369-383.

Ng et. al., "The pathological spectrum of diffuse axonal injury in blunt head trauma: assessment with axon and myelin stains," Clin Neurol Neurosurg (1994) 96:24-31.

Niebroj-Dobosz et al., "Immunochemical analysis of some proteins in cerebrospinal fluid and serum of patients with ischemic strokes," Folia Neuropathol (1994) 32(3):129-137.

Notice of Appeal, for Opposition for EP 09807153.3, dated Sep. 24, 2021, 5 pages.

Okazaki et al, "Pathogenic roles of cardiac autoantibodies in dilated cardiomyopathy," Trends in Molecular Medicine (2005) 11(7):322-326.

Park et al., "The generation of a 17 kDa neurotoxic fragment: an alternative mechanism by which tau mediates beta-amyloid-induced neurodegeneration," J Neurosci (2005) 25(22):5365-5375.

Pettigrew et al., "Microtubular Proteolysis in Focal Cerebral Ischema," J Cereb Blood Flow Metab (1996) 16(6):1189-1201.

Pettus et al., "Traumatically induced altered membrane permeability: its relationship to traumatically induced reactive axonal change," J Neurotrauma (1994) 11(5):507-522.

Pike et al., "Accumulation of Calpain and Caspase-3 Proteolytic Fragments of Brain-Derived alpha-II-Spectrin in Cerebral Spinal Fluid After Middle Cerebral Artery Occlusion in Rats," J Cereb Blood Flow Metab (2004) 24(1):98-106.

Pike et al., "Regional calpain and caspase-3 proteolysis of alpha-spectrin after traumatic brain injury," NeuroReport (1998) 9(11):2437-2442.

Quintana et al., "Antigen microarrays identify CNS-produced autoantibodies in RRMS," Neurology (2012) 78(8):532-539.

Rainer et al., "Effects of Filtration on Glyceraldehyde-3-Phosphate Dehydrogenase mRNA in the Plasma of Trauma Patients and Healthy Individuals," Clinical Chemistry (2004) 50(1):206-208.

Rainer et al., "Prognostic Use of Circulating Plasma Nucleic Acid Concentrations in Patients with Acute Stroke," Clinical Chemistry (2003) 49(4):562-569.

Rao et al., "Marked calpastatin (CAST) depletion in Alzheimer's disease accelerates cytoskeleton disruption and neurodegeneration: neuroprotection by CAST overexpression," J Neurosci (2008) 28(47):12241-12254.

Redell et al., "Traumatic brain injury alters expression of hippocampal microRNAs: Potential regulators of multiple pathophysiological processes," J Neurosci Res (2009) 87(6):1435-1448.

Response to Appeal, for Opposition for EP 09807153.3, dated Apr. 19, 2022, 89 pages.

Rissman et. al., "Caspase-cleavage of tau is an early event in Alzheimer disease tangle pathology," J Clin Invest (2004) 114:121-130.

Roche, Instruction Manual for "DIG Detection ELISA (ABTS)" and "DIG Detection ELISA (TMB)", Version 2, Nov. 1999, retrieved from http://jenobiotech.com/techsupport/protocol/ELISA1-17.pdf on Apr. 25, 2014, 18 pages.

Rohn et al., "Caspase-9 Activation and Caspase Cleavage of tau in the Alzheimer's Disease Brain," Neurobiol Dis (2002) 11(2):341-354.

Rudehill et al., "Autoreactive antibodies against neurons and basal lamina found in serum following experimental brain contusion in rats," Acta Neurochirurgica (2006) 148(2):199-205.

Saatman et al., "Behavioral efficacy of posttraumatic calpain inhibition is not accompanied by reduced spectrin proteolysis, cortical lesion, or apoptosis," J Cereb Blood Flow Metab (2000) 20(1):66-73.

Saatman et al., "Calpain inhibitor AK295 attenuates motor and cognitive deficits following experimental brain injury in the rat," Proc Natl Acad Sci (1996) 93(8):3428-3433.

Shimohama et al., "Changes in caspase expression in Alzheimer's disease: comparison with development and aging," Biochem Biophys Res Commun (1999) 256(2):381-384.

Silber et al., "Patients with progressive multiple sclerosis have elevated antibodies to neurofilament subunit," Neurology (2002) 58:1372-1381.

Silva et. al., "Presence of Tumor DNA in Plasma of Breast Cancer Patients: Clinicopathological Correlations," Cancer Research (1999) 59:3251-3256.

Siman et al., "Proteins released from degenerating neurons are surrogate markers for acute brain damage," Neurobiol Dis (2004) 16(2):311-320.

Singh et al., "Detection of brain autoantibodies in the serum of patients with Alzheimer's disease but not Down's syndrome," Immunol Lett (1986) 12(5-6):277-280.

Sinjoanu et al., "The novel calpain inhibitor A-705253 potently inhibits oligomeric beta-amyloid-induced dyanmin 1 and tau cleavage in hippocampal neurons," Neurochem Int (2008) 53(3-4):79-88.

Skoda et al., "Antibody formation against beta-tubulin class III in response to brain trauma," Brain Research Bulletin (2006) 68(4):213-216.

Smith et al., "Functional subsets of human helper-inducer cells defined by a new monoclonal antibody, UCHL1," Immunology. (1986) 58(1): 63-70.

Sorokina et al., "Autoantibodies to glutamate receptors and metabolic products of nitric oxide in blood serum of children in the acute period of brain trauma," Zh Nevrol Psikhiatr Im S S Korsakova (2008) 108(3):67-72.

Stagg et al., "Autoantibodies to glutamic acid decarboxylase in patients with epilepsy are associated with low cortical GABA levels," Epilepsia (2010) 51(9):1989-1901.

Statement of grounds of appeal, for Opposition for EP 09807153.3, dated Nov. 24, 2021, 39 pages.

Svetlov et al., "Biomarkers of Blast-induced neurotrauma: profiling molecular and cellular mechanisms of Blast brain injury," Journal of Neurotrauma (2009) 26:913-921.

Svetlov et al., "Title: Pathological Fingerprints, Systems Biology and Biomarkers of Blast Brain Injury", 2010, Retrieved from the Internet: URL:http:jjwww.dtic.mil/dticjtr/fulltextju2/a548699.pdf, p. 4-6.

Taback et al., "Circulating Nucleic Acids and Proteomics of Plasma/Serum Clinical Utility," Annals of the New York Academy of Sciences (2004) 1022:1-8.

Tan et al., "Deoxyribonucleic Acid (DNA) and Antibodies to DNA in the Serum of Patients with Systemic Lupus Erythematosus," Journal of Clinical Investigation (1966) 45(11):1732-1740.

(56) References Cited

OTHER PUBLICATIONS

Tanriverdi et al., "Antipituitary antibodies after traumatic brain injury: is head trauma-induced pituitary dysfunction associated with autoimmunity?" Eur J of Endocrinol (2008) 159(1):7-13.
Terryberry et al., "Autoantibodies in Neurodegenerative Diseases: Antigen-Specific Frequencies and Intrathecal Analysis," Neurobiology of Aging (1998) 19(3):205-216.
Terryberry et al., "Clinical Utility of Autoantibodies in Guillain-Barre Syndrome and Its Variants," Clinical Reviews in Allergy and Immunology (1998) 16:265-273.
The SAFE Study Investigators, "Saline or Albumin for Fluid Resuscitation in Patients with Traumatic Brain Injury," N Engl J Med (2007) 357:874-884.
Turner et al., "Expression of COX2, HO1, and GFAP following collagenase-induced intracerebral hemorrhage," Neurology (2000) 54:A299.
Uryu et al., "Multiple proteins implicated in neurodegenerative diseases accumulate in axons after brain trauma in humans", Exp Neurol (2007) 208(2):185-192.
Van Geel et al., :An enzyme immunoassay to quantify neurofilament light chain in cerebrospinal fluid, J. Immunol. Methods (2005) 296:179-185.
Verbeek et al., "Accumulation of intercellular adhesion loecule-1 in senile plaques in brain tissue of patients with Alzheimer's disease," American Journal of Pathology (1994) 144(1):104-116.
Vissers et al., "Rapid immunoassay for the determination of glial fibrillary acidic protein (GFAP) in serum," Clin Chim Acta (2006) 366(1-2):336-340.
Walker et al., "DNA-based molecular diagnostic techniques: research needs for standardization and validation of the detection of aquatic animal pathogen and diseases," Report and proceedings of the joint FAO/NACA/CSIRO/ACIAR/DFID expert workshop. Bangkok, Thailand, Feb. 7-9, 1999. FAO Fisheries Technical Paper No. 395 Rome, FAO, 2000, pp. i-iv & 30-37.
Wang et al., "Calpain and caspase: can you tell the difference?" Trends Neurosci (2000) 23(1):20-26.
Wang et al., "Simultaneous Degradation of αII and βII-Spectrin by Caspase 3 (CPP32) in Apoptotic Cells," J Biol Chem (1998) 273(35):22490-22497.
Wang, et al., "Proteomic identification of biomarkers of traumatic brain injury," Expert Rev Proteomics (2005) 2(4):603-614.
Warren et al., "Calpain- and caspase-mediated αII-spectrin and tau proteolysis in rat cerebrocortical neuronal cultures after ecstasy or methamphetamine exposure," Intl J Neuro-Psychopharmocology, (2007) 10(4):479-489.
Warren et al., "Concurrent calpain and caspase-3 mediated proteolysis of alphaII-spectrin and tau in rat brain after methamphetamine exposure: A similar profile to traumatic brain injury," Life Sciences (2005) 78(3):301-309.
Wilhelm et al., "Immune reactivity towards insulin, its amyloid and protein S100B in blood sera of Parkinson's disease patients," Eur J Neurol (2007) 14(3):327-334.
Yang et al., "Calpain-Induced Proteolysis of Normal Human Tau and Tau Associated with Paired Helical Filaments," Eur J Biochem (1995) 223(1):9-17.
Yang et al., "Electrochemiluminescence: A New Diagnostics and Research Tool," Bio/Technology, vol. 12, Feb. 1994, p. 193-194.
Yen et al., "FTDP-17 tau mutations decrease the susceptibility of tau to calpain I digestion," FEBS Lett (1999) 461(1):91-95.
Yokota et al., "Three distinct phases offodrin proteolysis induced in postischemic hippocampus—involvement of calpain and unidentified protease," Stroke (1995) 26(10):1901-1907.
Yoshiyama et al., "Enhanced neurofibrillary tangle formation, cerebral atrophy, and cognitive deficits induced by repetitive mild brain injury in a transgenic tauopathy mouse model" J Neurotrama (2005) 22(10):1134-1141.
Zemlan et al., "C-tau biomarker of neuronal damage in severe brain injured patients: association with elevated intracranial pressure and clinical outcome," Brain Res (2002) 947(1):131-139.
Zemlan et al., "Quantification and localization of kainic acid-induced neurotoxicity employing a new biomarker of cell death: cleaved microtubule associated protein-tau (C-tau)," Neuroscience (2003) 121(2):399-409.
Zhang et al., "Inhibition of autophagy causes tau proteolysis by activating calpain in rat brain," J Alzheimers Dis (2009) 16(1):39-47.
Zhang et al., "Multiple alphaII-spectrin breakdown products distinguish calpain and caspase dominated necrotic and apoptotic cell death pathways," Apoptosis (2009) 14(11):1289-1298.
Zhang et al., "Roles of autoantibodies in central nervous system injury," Discov Med (2011) 11(60):395-402.
Zhang et al., "Expression of glial fibrillary acidic protein in pericerebral hemorrhage foci," Journal of the Fourth Military Medical University (Di-si Junyi Daxue Xuebao) (2003) 24(17):1586-1588.
Zhao et al., "Maitotoxin Induces Calpain But Not Caspase-3 Activation and Necrotic Cell Death in Primary Septo-Hippocampal Cultures," Neurochem Res (1999) 24(3):371-382.
Zhu et al., "Non-invasive imaging of GFAP expression after neuronal damage in mice," Neurosci Letters (2004) 367(2):210-212.

\* cited by examiner

A

B

A

B

ROC analysis of UCH-L1, GFAP and SBDP145 in human CSF (severe TBI vs. Control A) First 24 hours post-injury Elevation of brain injury biomarkers (GFAP, UCH-L1 and MAP2) in plasma in stroke patients.

BIOMARKER DETECTION PROCESS AND ASSAY OF NEUROLOGICAL CONDITION

CROSS REFERENCE TO RELATED APPLICATIONS

This application is a continuation of U.S. patent application Ser. No. 15/709,368, filed Sep. 19, 2017, which is continuation of U.S. patent application Ser. No. 13/058,748, filed Feb. 11, 2011, which is a national stage entry of Patent Cooperation Treaty Application Serial No. PCT/US2009/053376, filed Aug. 11, 2009, which claims priority to U.S. Provisional Application No. 61/188,554 filed Aug. 11, 2008; U.S. Provisional Application No. 61/097,622 filed Sep. 17, 2008; U.S. Provisional Application No. 61/218,727 filed Jun. 19, 2009; and U.S. Provisional Application No. 61/271,135 filed Jul. 18, 2009. The contents of each related applications are incorporated herein in their entirety.

GOVERNMENTAL SUPPORT

Portions of this work were supported by grants N14-06-1-1029, W81XWH-8-1-0376 and W81XWH-07-01-0701 from the United States Department of Defense.

FIELD OF THE INVENTION

The present invention in general relates to determination of neurological condition of an individual and in particular to measuring the quantity of a neuroprotective biomarker such as glial fibrillary acidic protein (GFAP) in concert with another biomarker of neurological condition.

BACKGROUND OF THE INVENTION

The field of clinical neurology remains frustrated by the recognition that secondary injury to a central nervous system tissue associated with physiologic response to the initial insult could be lessened if only the initial insult could be rapidly diagnosed or in the case of a progressive disorder before stress on central nervous system tissues reached a preselected threshold. Traumatic, ischemic, and neurotoxic chemical insult, along with generic disorders, all present the prospect of severe brain damage. While the diagnosis of severe forms of each of these causes of brain damage is straightforward through clinical response testing, computed tomography (CT), and magnetic resonance imaging (MRI), the imaging diagnostics are limited by both the high cost of spectroscopic imaging and long diagnostic time. The clinical response testing of incapacitated individuals is of limited value and often precludes a nuanced diagnosis. Additionally, owing to the limitations of existing diagnostics, situations arise wherein a subject experiences a stress to their neurological condition but are often unaware that damage has occurred or fail seek treatment as the subtle symptoms often quickly resolve. The lack of treatment of these mild to moderate challenges to neurologic condition of a subject can have a cumulative effect or otherwise result in a severe brain damage event, either of which have a poor clinical prognosis.

In order to overcome the limitations associated with spectroscopic and clinical response diagnosis of neurological condition, there is increasing attention on the use of biomarkers as internal indicators of change to molecular or cellular level health condition of a subject. As biomarker detection uses a sample obtained from a subject, typically cerebrospinal fluid, blood, or plasma, and detects the biomarkers in that sample, biomarker detection holds the prospect of inexpensive, rapid, and objective measurement of neurological condition. The attainment of rapid and objective indicators of neurological condition allows one to determine severity of a non-normal brain condition with a previously unrealized degree of objectivity, predict outcome, guide therapy of the condition, as well as monitor subject responsiveness and recovery. Additionally, such information as obtained from numerous subjects allows one to gain a degree of insight into the mechanism of brain injury.

A number of biomarkers have been identified as being associated with severe traumatic brain injury as is often seen in vehicle collision and combat wounded subjects. These biomarkers included spectrin breakdown products such as SBDP150, SBDP150i, SBDP145 (calpain mediated acute neural necrosis), SBDP120 (caspase mediated delayed neural apoptosis), UCH-L1 (neuronal cell body damage marker), and MAP2 dendritic cell injury associated marker. The nature of these biomarkers is detailed in U.S. Pat. Nos. 7,291,710 and 7,396,654, the contents of which are hereby incorporated by reference.

Glial Fibrillary Acidic Protein (GFAP), a member of the cytoskeletal protein family, is the principal 8-9 nanometer intermediate filament of glial cells such as mature astrocytes of the central nervous system (CNS). GFAP is a monomeric molecule with a molecular mass between 40 and 53 kDa and an isoelectric point between 5.7 and 5.8. GFAP is highly brain specific protein that is not found outside the CNS. GFAP is released into the blood and CSF soon after brain injury. In the CNS following injury, either as a result of trauma, disease, genetic disorders, or chemical insult, astrocytes become reactive in a way that is characterized by rapid synthesis of GFAP termed astrogliosis or gliosis. However, GFAP normally increases with age and there is a wide variation in the concentration and metabolic turnover of GFAP in brain tissue.

Thus, there exists a need for a process and an assay for providing improved measurement of neurological condition through the quantification of a first biomarker such as GFAP in combination with another biomarker associated with neurological condition.

SUMMARY OF THE INVENTION

A process for determining the neurological condition of a subject or cells from the subject includes measuring a sample obtained from the subject or cells from the subject at a first time for a quantity of a first biomarker selected from the group of GFAP, UCH-L1, NSE, MAP2, or SBDP. The sample is also measured for a quantity of at least one additional neuroactive biomarker. Through comparison of the quantity of the first biomarker and the quantity of the at least one additional neuroactive biomarker to normal levels for each biomarker, the neurological condition of the subject is determined. When the subject have been exposed to an event that could cause mild traumatic brain injury and moderate traumatic brain injury, a process of measuring UCH-L1 and GFAP, such injuries have detection cutoffs for UCH-L1 and GFAP in serum of 0.39 nanograms per milliliter (ng/ml) and 1.4 ng/ml, respectively.

An assay for determining the neurological condition of a subject or neural cells from the subject is also provided. The assay includes: (a) a substrate for holding a sample isolated from a subject or the cells; (b) a first biomarker specifically binding agent wherein a first biomarker is one of GFAP, UCH-L1, NSE, MAP2, or SBDP; (c) a binding agent specific for another neuroactive biomarker (including one of GFAP, UCH-L1, NSE, MAP2, or SBDP not chosen as the first biomarker); and (d) printed instructions for reacting the first biomarker specific agent with a first portion of the sample so as to detect an amount of said first biomarker and reacting said at least one additional neuroactive biomarker specific agent with a second portion of the sample and the at least one additional neuroactive biomarker in the sample so as to detect an amount of said at least one additional neuroactive biomarker for relation to the condition of the subject or cells derived the subject.

A process for determining if a subject has suffered mild traumatic brain injury or moderate traumatic brain injury in an event is provided that includes measuring a sample obtained from the subject or cells from the subject at a first time after the event for a quantity of GFAP. By comparing the quantity of GFAP to normal levels of GFAP in a control, one determines if the subject has suffered mild traumatic brain injury or moderate traumatic brain injury in the event.

DETAILED DESCRIPTION OF THE PREFERRED EMBODIMENTS

Figure 1:
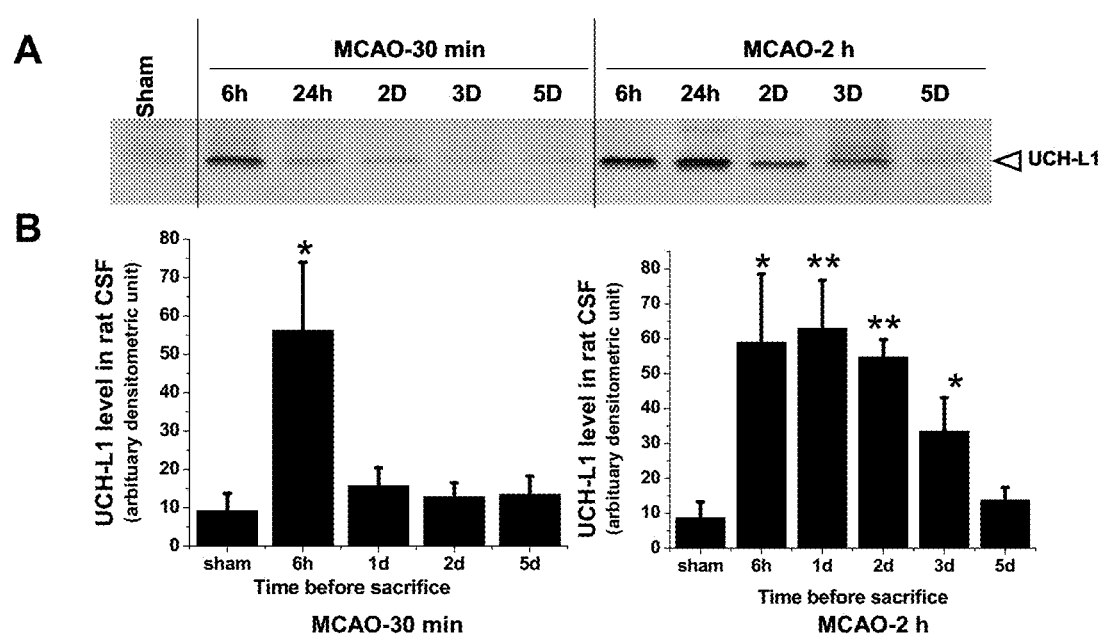
FIG. 1 represents quantitative western blotting of UCH-L1 in rat CSF following MCAO.

The present invention has utility in the diagnosis and management of abnormal neurological condition. Through the measurement of a biomarker such as GFAP from a subject in combination with values obtained for an additional neuroactive biomarker, a determination of subject neurological condition is provided with greater specificity than previously attainable. The present description is directed toward a first biomarker of GFAP for illustrative purposes only and is not meant to be a limitation on the practice or scope of the present invention. It is appreciated that the invention encompasses several other first and additional biomarkers illustratively including UCH-L1, NSE, MAP2, and SBDP. The description is appreciated by one of ordinary skill in the art as fully encompassing all inventive biomarkers as an inventive first biomarker as described herein. Surprisingly, by combining the detection of more than one biomarker, a synergistic result is achieved. Illustratively, combining the detection of two neuroactive biomarkers such as UCH-L1 and GFAP provides sensitive detection that is unexpectedly able to discern the level and severity of an abnormal neurological condition in a subject.

The present invention provides for the detection of a neurological condition in a subject. A neurological condition may be an abnormal neurological condition such as that caused by genetic disorder, injury, or disease to nervous tissue. As such, it is a further object of the present invention to provide a means for detecting or diagnosing an abnormal neurological condition in a subject.

The present invention also provides an assay for detecting or diagnosing the neurological condition of a subject. As the neurological condition may be the result of stress such as that from exposure to environmental, therapeutic, or investigative compounds, it is a further aspect of the present invention to provide a process and assay for screening candidate drug or other compounds or for detecting the effects of environmental contaminants regardless of whether the subject itself or cells derived there from are exposed to the drug candidate or other possible stressors.

For purposes of the subject invention, brain injury is divided into two levels, mild traumatic brain injury (MTBI), and traumatic brain injury (TBI). An intermediate level of moderate TBI is also referred to herein. The spectrum between MTBI and extending through moderate TBI is also referred to synonymously mild to moderate TBI or by the abbreviation MMTBI. TBI is defined as an injury that correlates with a two-fold increase or greater of two-fold decrease or greater in molecular marker levels or activities. MTBI is defined and an injury that correlates with less than a two-fold increase or two-fold decrease in molecular marker levels or activities.

An inventive process preferably includes determining the neurological condition of a subject by assaying a sample derived from a subject at a first time for the presence of a first biomarker. A biomarker is a cell, protein, nucleic acid, steroid, fatty acid, metabolite, or other differentiator useful for measurement of biological activity or response. Biomarkers operable herein illustratively include: ubiquitin carboxyl-terminal esterase, ubiquitin carboxy-terminal hydrolase, spectrin breakdown product(s), a neuronally-localized intracellular protein, MAP-tau, C-tau, MAP2, poly (ADP-ribose) polymerase (PARP), collapsin response mediator protein, Annexin A11, Aldehyde dehydrogenase family 7, Cofilin 1, Profilin 1, α-Enolase (non-neural enolase), Enolase 1 protein, Glyceraldehyde-3-phosphate dehydrogenase, Hexokinase 1, Aconitase 2, Acetyl-CoA synthetase 2, Neuronal protein 22, Phosphoglycerate kinase 2, Phosphoglycerate kinase 1, Hsc70-ps1, Glutamate dehydrogenase 1, Aldolase A, Aldolase C, fructose-biphosphate, Dimethylarginine dimethylaminohydrolase 1, Microtubule-associated protein 2, Carbonic anhydrase, ADP-ribosylation factor 3, Transferrin, Liver regeneration-related protein, Hemoglobin α-chain, Hemoglobin β chain, Liver regeneration-related protein, Fetuin β, 3-Oxoacid-CoA transferase, Malate dehydrogenase 1, NAD (soluble), Lactate dehydrogenase B, Malate dehydrogenase, Carboxylesterase E1 precursor, Serine protease inhibitor α1, Haptoglobin, Ubiquitin carboxyl-terminal hydrolase L1, Serine protease inhibitor 2a, T-kininogen, α1 major acute phase protein, Albumin, α1 major acute phase protein prepeptide, Murinoglobulin 1 homolog, Group-specific component protein, Guanosine diphosphate dissociation inhibitor 1, Collapsin response mediator protein 2, Murinoglobulin 1 homolog, Ferroxidase, Ceruloplasmin, Spectrin α-chain, brain, C-reactive protein, Brain creatine kinase, Proteasome subunit α-type 7, 14-3-3 protein, Synaptotagmin, subtypes thereof, fragments thereof, breakdown products thereof, or combinations thereof. Other potential biomarkers illustratively include those identified by Kobeissy, F H, et al, *Molecular & Cellular Proteomics,* 2006; 5:1887-1898, the contents of which are incorporated herein by reference, or others known in the art.

A first biomarker is preferably a neuroactive biomarker. Illustrative examples of neuroactive biomarkers include GFAP, ubiquitin carboxyl-terminal hydrolase L1 (UCH-L1), Neuron specific enolase (NSE), spectrin breakdown products (SBDP), preferably SBDP150, SBDP150i SBDP145, SBDP120, S100 calcium binding protein B (S100b), microtubule associated proteins (MAP), preferably MAP2, MAP1, MAP3, MAP4, MAP5, myelin basic protein (MBP), Tau, Neurofilament protein (NF), Cannabinoid Receptor (CB), CAM proteins, Synaptic protein, collapsin response mediator proteins (CRMP), inducible nitric oxide synthase (iNOS), Neuronal Nuclei protein (NeuN), 2',3'-cyclic nucleotide-3'-phosphohydrolase (CNPase), Neuroserpin, alpha-internexin, microtubule-associated protein 1 light chain 3 (LC3), Neurofascin, the glutamate transporters (EAAT), Nestin, Cortin-1, 2', and BIII-Tubulin.

The inventive process also includes assaying the sample for at least one additional neuroactive biomarker. The one additional neuroactive biomarker is preferably not the same biomarker as the first biomarker. Any of the aforementioned inventive biomarkers are operable as an additional neuroactive biomarker. Any number of biomarkers can be detected such as 2, 3, 4, 5, 6, 7, 8, 9, 10, or more. Detection can be either simultaneous or sequential and may be from the same biological sample or from multiple samples from the same or different subjects. Preferably, detection of multiple biomarkers is in the same assay chamber. The inventive process further includes comparing the quantity of the first biomarker and the quantity of the at least one additional neuroactive biomarker to normal levels of each of the first biomarker and the one additional neuroactive biomarker to determine the neurological condition of the subject.

In a preferred embodiment a biomarker is GFAP. GFAP is associated with glial cells such as astrocytes. Preferably, an additional neuroactive biomarker is associated with the health of a different type of cell associated with neural function. For example, CNPase is found in the myelin of the central nervous system, and NSE is found primarily in neurons. More preferably, the other cell type is an axon, neuron, or dendrite.

In another preferred embodiment, especially for MBTI and MMTBI, is UCH-L1 in combination with other biomarkers such as GFAP and MAP2.

It is appreciated however, that multiple biomarkers may be predictors of different modes or types of damage to the same cell type. Through the use of an inventive assay inclusive of biomarkers associated with glial cells as well as at least one other type of neural cell, the type of neural cells being stressed or killed as well as quantification of neurological condition results provides rapid and robust diagnosis of traumatic brain injury type. Measuring GFAP along with at least one additional neuroactive biomarker and comparing the quantity of GFAP and the additional biomarker to normal levels of the markers provides a determination of subject neurological condition.

Preferably, specific biomarker levels that when measured in concert with GFAP afford superior evaluation of subject neurological condition include SBDP 150, SBDP150i, a combination of SBDP145 (calpain mediated acute neural necrosis) and SBDP120 (caspase mediated delayed neural apoptosis), UCH-L1 (neuronal cell body damage marker), and MAP2. This is noted to be of particular value in measuring MMTBI and screening drug candidates or other neural cell stressor compounds with cell cultures.

A sample is preferably a biological sample. Preferred examples of biological samples are illustratively cells, tissues, cerebral spinal fluid (CSF), artificial CSF, whole blood, serum, plasma, cytosolic fluid, urine, feces, stomach fluids, digestive fluids, saliva, nasal or other airway fluid, vaginal fluids, semen, buffered saline, saline, water, or other biological fluid recognized in the art. Most preferably, a biological sample is CSF or blood serum. It is appreciated that two or more separate biological samples are optionally assayed to elucidate the neurological condition of the subject.

In addition to increased cell expression, biomarkers also appear in biological fluids in communication with injured cells. Obtaining biological fluids such as cerebrospinal fluid (CSF), blood, plasma, serum, saliva and urine, from a subject is typically much less invasive and traumatizing than obtaining a solid tissue biopsy sample. Thus, samples that are biological fluids are preferred for use in the invention. CSF, in particular, is preferred for detecting nerve damage in a subject as it is in immediate contact with the nervous system and is readily obtainable. Serum is a preferred biological sample as it is easily obtainable and presents much less risk of further injury or side-effect to a donating subject.

To provide correlations between neurological condition and measured quantities of GFAP and other neuroactive biomarkers, samples of CSF or serum are collected from subjects with the samples being subjected to measurement of GFAP as well as other neuroactive biomarkers. The subjects vary in neurological condition. Detected levels of GFAP and other neuroactive biomarkers are optionally then correlated with CT scan results as well as GCS scoring. Based on these results, an inventive assay is developed and validated (Lee et al., Pharmacological Research 23:312-328, 2006). It is appreciated that GFAP and other neuroactive biomarkers, in addition to being obtained from CSF and serum, are also readily obtained from blood, plasma, saliva, urine, as well as solid tissue biopsy. While CSF is a preferred sampling fluid owing to direct contact with the nervous system, it is appreciated that other biological fluids have advantages in being sampled for other purposes and therefore allow for inventive determination of neurological condition as part of a battery of tests performed on a single sample such as blood, plasma, serum, saliva or urine.

A biological sample is obtained from a subject by conventional techniques. For example, CSF is preferably obtained by lumbar puncture. Blood is preferably obtained by venipuncture, while plasma and serum are obtained by fractionating whole blood according to known methods. Surgical techniques for obtaining solid tissue samples are well known in the art. For example, methods for obtaining a nervous system tissue sample are described in standard neurosurgery texts such as Atlas of Neurosurgery: Basic Approaches to Cranial and Vascular Procedures, by F. Meyer, Churchill Livingstone, 1999; Stereotactic and Image Directed Surgery of Brain Tumors, 1st ed., by David G. T. Thomas, W B Saunders Co., 1993; and Cranial Microsurgery: Approaches and Techniques, by L. N. Sekhar and E. De Oliveira, 1st ed., Thieme Medical Publishing, 1999. Methods for obtaining and analyzing brain tissue are also described in Belay et al., Arch. Neurol. 58: 1673-1678 (2001); and Seijo et al., J. Clin. Microbiol. 38: 3892-3895 (2000).

After insult, nerve cells in in vitro culture or in situ in a subject express altered levels or activities of one or more proteins than do such cells not subjected to the insult. Thus, samples that contain nerve cells, e.g., a biopsy of a central nervous system or peripheral nervous system tissue are illustratively suitable biological samples for use in the invention. In addition to nerve cells, however, other cells express illustratively $\alpha$II-spectrin including, for example, cardiomyocytes, myocytes in skeletal muscles, hepatocytes, kidney cells and cells in testis. A biological sample including such cells or fluid secreted from these cells might also be used in an adaptation of the inventive methods to determine and/or characterize an injury to such non-nerve cells.

A subject illustratively includes a dog, a cat, a horse, a cow, a pig, a sheep, a goat, a chicken, non-human primate, a human, a rat, and a mouse. Subjects who most benefit from the present invention are those suspected of having or at risk for developing abnormal neurological conditions, such as victims of brain injury caused by traumatic insults (e.g., gunshot wounds, automobile accidents, sports accidents, shaken baby syndrome), ischemic events (e.g., stroke, cerebral hemorrhage, cardiac arrest), neurodegenerative disorders (such as Alzheimer's, Huntington's, and Parkinson's diseases; prion-related disease; other forms of dementia), epilepsy, substance abuse (e.g., from amphetamines, Ecstasy/MDMA, or ethanol), and peripheral nervous system pathologies such as diabetic neuropathy, chemotherapy-induced neuropathy and neuropathic pain.

Baseline levels of several biomarkers are those levels obtained in the target biological sample in the species of desired subject in the absence of a known neurological condition. These levels need not be expressed in hard concentrations, but may instead be known from parallel control experiments and expressed in terms of fluorescent units, density units, and the like. Typically, in the absence of a neurological condition SBDPs are present in biological samples at a negligible amount. However, UCH-L1 is a highly abundant protein in neurons. Determining the baseline levels of UCH-L1 in neurons of particular species is well within the skill of the art. Similarly, determining the concentration of baseline levels of MAP2, GFAP, NSE, or other biomarker is well within the skill of the art.

As used herein the term "diagnosing" means recognizing the presence or absence of a neurological or other condition such as an injury or disease. Diagnosing is optionally referred to as the result of an assay wherein a particular ratio or level of a biomarker is detected or is absent.

As used herein a "ratio" is either a positive ratio wherein the level of the target is greater than the target in a second sample or relative to a known or recognized baseline level of the same target. A negative ratio describes the level of the target as lower than the target in a second sample or relative to a known or recognized baseline level of the same target. A neutral ratio describes no observed change in target biomarker.

As used herein an injury is an alteration in cellular or molecular integrity, activity, level, robustness, state, or other alteration that is traceable to an event. Injury illustratively includes a physical, mechanical, chemical, biological, functional, infectious, or other modulator of cellular or molecular characteristics. An event is illustratively, a physical trauma such as an impact (percussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

An injury is optionally a physical event such as a percussive impact. An impact is the like of a percussive injury such as resulting to a blow to the head that either leaves the cranial structure intact or results in breach thereof. Experimentally, several impact methods are used illustratively including controlled cortical impact (CCI) at a 1.6 mm depression depth, equivalent to severe TBI in human. This method is described in detail by Cox, C D, et al., *J Neurotrauma*, 2008; 25(11):1355-65. It is appreciated that other experimental methods producing impact trauma are similarly operable.

TBI may also result from stroke. Ischemic stroke is optionally modeled by middle cerebral artery occlusion (MCAO) in rodents. UCH-L1 protein levels, for example, are increased following mild MCAO which is further increased following severe MCAO challenge. Mild MCAO challenge may result in an increase of protein levels within two hours that is transient and returns to control levels within 24 hours. In contrast, severe MCAO challenge results in an increase in protein levels within two hours following injury and may be much more persistent demonstrating statistically significant levels out to 72 hours or more.

An exemplary process for detecting the presence or absence of GFAP and one or more other neuroactive biomarkers in a biological sample involves obtaining a biological sample from a subject, such as a human, contacting the biological sample with a compound or an agent capable of detecting of the marker being analyzed, illustratively including an antibody or aptamer, and analyzing binding of the compound or agent to the sample after washing. Those samples having specifically bound compound or agent express the marker being analyzed.

An inventive process can be used to detect GFAP and one or more other neuroactive biomarkers in a biological sample in vitro, as well as in vivo. The quantity of GFAP and one or more other neuroactive biomarkers in a sample is compared with appropriate controls such as a first sample known to express detectable levels of the marker being analyzed (positive control) and a second sample known to not express detectable levels of the marker being analyzed (a negative control). For example, in vitro techniques for detection of a marker illustratively include enzyme linked immunosorbent assays (ELISAs), radioimmuno assay, radioassay, western blot, Southern blot, northern blot, immunoprecipitation, immunofluorescence, mass spectrometry, RT-PCR, PCR, liquid chromatography, high performance liquid chromatography, enzyme activity assay, cellular assay, positron emission tomography, mass spectroscopy, combinations thereof, or other technique known in the art. Furthermore, in vivo techniques for detection of a marker include introducing a labeled agent that specifically binds the marker into a biological sample or test subject. For example, the agent can be labeled with a radioactive marker whose presence and location in a biological sample or test subject can be detected by standard imaging techniques. Optionally, the first biomarker specifically binding agent and the agent specifically binding at least one additional neuroactive biomarker are both bound to a substrate. It is appreciated that a bound agent assay is readily formed with the agents bound with spatial overlap, with detection occurring through discernibly different detection for first biomarker and each of at least one additional neuroactive biomarkers. A color intensity based quantification of each of the spatially overlapping bound biomarkers is representative of such techniques.

Any suitable molecule that can specifically bind GFAP and any suitable molecule that specifically binds one or more other neuroactive biomarkers are operative in the invention to achieve a synergistic assay. A preferred agent for detecting GFAP or the one or more other neuroactive biomarkers is an antibody capable of binding to the biomarker being analyzed. Preferably, an antibody is conjugated with a detectable label. Such antibodies can be polyclonal or monoclonal. An intact antibody, a fragment thereof (e.g., Fab or F(ab')$_2$), or an engineered variant thereof (e.g., sFv) can also be used. Such antibodies can be of any immunoglobulin class including IgG, IgM, IgE, IgA, IgD and any subclass thereof. Antibodies for numerous inventive biomarkers are available from vendors known to one of skill in the art. Illustratively, antibodies directed to inventive biomarkers are available from Santa Cruz Biotechnology (Santa Cruz, CA). Exemplary antibodies operative herein to detect a first biomarker include anti-GFAP antibody, anti-UCH-L1 antibody, anti-NSE antibody, anti-MAP2 antibody, or an anti-SBDP antibody. Other biomarkers to be targeted as part of an inventive assay different from the first biomarker include GFAP, NSE, SBDP, SBDP150, SBDP145, SBDP120, S100b, MAP2, MAP1, MAP3, MAP4, MAP5, MBP, Tau, Neurofilament protein (NF), Cannabinoid Receptor CB, CAM, Synaptic protein, CRMP, iNOS, NeuN, CSPase, Neuroserpin, alpha-internexin, LC3, Neurofascin, EAAT, Nestin, Cortin-1, or BIII-Tubulin An antibody is optionally labeled. A person of ordinary skill in the art recognizes numerous labels operable herein. Labels and labeling kits are commercially available optionally from Invitrogen Corp, Carlsbad, CA Labels illustratively include, fluorescent labels, biotin, peroxidase, radionucleotides, or other label known in the art. Alternatively, a detection species of another antibody or other compound known to the art is used as form detection of a biomarker bound by an antibody.

Antibody-based assays are preferred for analyzing a biological sample for the presence of GFAP and one or more other neuroactive biomarkers. Suitable western blotting methods are described below in the examples section. For more rapid analysis (as may be important in emergency medical situations), immunosorbent assays (e.g., ELISA and RIA) and immunoprecipitation assays may be used. As one example, the biological sample or a portion thereof is immobilized on a substrate, such as a membrane made of nitrocellulose or PVDF; or a rigid substrate made of polystyrene or other plastic polymer such as a microtiter plate, and the substrate is contacted with an antibody that specifically binds GFAP, or one of the other neuroactive biomarkers under conditions that allow binding of antibody to the biomarker being analyzed. After washing, the presence of the antibody on the substrate indicates that the sample contained the marker being assessed. If the antibody is directly conjugated with a detectable label, such as an enzyme, fluorophore, or radioisotope, the presence of the label is optionally detected by examining the substrate for the detectable label. Alternatively, a detectably labeled secondary antibody that binds the marker-specific antibody is added to the substrate. The presence of detectable label on the substrate after washing indicates that the sample contained the marker.

Numerous permutations of these basic immunoassays are also operative in the invention. These include the biomarker-specific antibody, as opposed to the sample being immobilized on a substrate, and the substrate is contacted with GFAP or another neuroactive biomarker conjugated with a detectable label under conditions that cause binding of antibody to the labeled marker. The substrate is then contacted with a sample under conditions that allow binding of the marker being analyzed to the antibody. A reduction in the amount of detectable label on the substrate after washing indicates that the sample contained the marker.

Although antibodies are preferred for use in the invention because of their extensive characterization, any other suitable agent (e.g., a peptide, an aptamer, or a small organic molecule) that specifically binds GFAP or another neuroactive biomarker is optionally used in place of the antibody in the above described immunoassays. For example, an aptamer that specifically binds αII spectrin and/or one or more of its SBDPs might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

A myriad of detectable labels that are operative in a diagnostic assay for biomarker expression are known in the art. Agents used in methods for detecting GFAP or another neuroactive biomarker are conjugated to a detectable label, e.g., an enzyme such as horseradish peroxidase. Agents labeled with horseradish peroxidase can be detected by adding an appropriate substrate that produces a color change in the presence of horseradish peroxidase. Several other detectable labels that may be used are known. Common examples of these include alkaline phosphatase, horseradish peroxidase, fluorescent compounds, luminescent compounds, colloidal gold, magnetic particles, biotin, radioisotopes, and other enzymes. It is appreciated that a primary/secondary antibody system is optionally used to detect one or more biomarkers. A primary antibody that specifically recognizes one or more biomarkers is exposed to a biological sample that may contain the biomarker of interest. A secondary antibody with an appropriate label that recognizes the species or isotype of the primary antibody is then contacted with the sample such that specific detection of the one or more biomarkers in the sample is achieved.

The present invention employs a step of correlating the presence or amount of GFAP alone, or with one or more other neuroactive biomarker in a biological sample with the severity and/or type of nerve cell injury. GFAP measurement alone is shown herein to be highly effective in detecting MMTBI. The amount of GFAP and one or more other neuroactive biomarkers in the biological sample are associated with a neurological condition such as traumatic brain injury as detailed in the examples. The results of an inventive assay to synergistically measure GFAP and one or more other neuroactive biomarkers can help a physician or veterinarian determine the type and severity of injury with implications as to the types of cells that have been compromised. These results are in agreement with CT scan and GCS results, yet are quantitative, obtained more rapidly, and at far lower cost.

The present invention provides a step of comparing the quantity of GFAP and the amount of at least one other neuroactive biomarker to normal levels to determine the neurological condition of the subject. It is appreciated that selection of additional biomarkers allows one to identify the types of cells implicated in an abnormal neurological condition as well as the nature of cell death in the case of an axonal injury marker, namely an SBDP. The practice of an inventive process provides a test which can help a physician determine suitable therapeutics to administer for optimal benefit of the subject. While the data provided in the examples herein are provided with respect to a full spectrum of traumatic brain injury, it is appreciated that these results are applicable to ischemic events, neurodegenerative disorders, prion related disease, epilepsy, chemical etiology and peripheral nervous system pathologies. As is shown in the subsequently provided example data, a gender difference is unexpectedly noted in abnormal subject neurological condition.

An assay for analyzing cell damage in a subject or a cell culture isolated therefrom is also provided. The assay includes: (a) a substrate for holding a sample isolated from a subject suspected of having a damaged nerve cell, the sample being a fluid in communication with the nervous system of the subject prior to being isolated from the subject; (b) a GFAP (or other biomarker) specific binding agent; (c) a binding agent specific for another neuroactive biomarker; and (d) printed instructions for performing the assay illustratively for reacting: the specific binding agent with the biological sample or a portion of the biological sample to detect the presence or amount of biomarker, and the agent specific for another neuroactive biomarker with the biological sample or a portion of the biological sample to detect the presence or amount of the at least one biomarker in the biological sample. The inventive assay can be used to detect a neurological condition for financial renumeration.

The assay optionally includes a detectable label such as one conjugated to the agent, or one conjugated to a substance that specifically binds to the agent, such as a secondary antibody.

An inventive process illustratively includes diagnosing a neurological condition in a subject, treating a subject with a neurological condition, or both. In a preferred embodiment an inventive process illustratively includes obtaining a biological sample from a subject. The biological sample is assayed by mechanisms known in the art for detecting or identifying the presence of one or more biomarkers present in the biological sample. Based on the amount or presence of a target biomarker in a biological sample, a ratio of one or more biomarkers is optionally calculated. The ratio is optionally the level of one or more biomarkers relative to the level of another biomarker in the same or a parallel sample, or the ratio of the quantity of the biomarker to a measured or previously established baseline level of the same biomarker in a subject known to be free of a pathological neurological condition. The ratio allows for the diagnosis of a neurological condition in the subject. An inventive process also optionally administers a therapeutic to the subject that will either directly or indirectly alter the ratio of one or more biomarkers.

An inventive process is also provided for diagnosing and optionally treating a multiple-organ injury. Multiple organs illustratively include subsets of neurological tissue such as brain, spinal cord and the like, or specific regions of the brain such as cortex, hippocampus and the like. Multiple injuries illustratively include apoptotic cell death which is detectable by the presence of caspase induced SBDPs, and oncotic cell death which is detectable by the presence of calpain induced SBDPs. The inventive process illustratively includes assaying for a plurality of biomarkers in a biological sample obtained from a subject wherein the biological was optionally in fluidic contact with an organ suspected of having undergone injury or control organ when the biological sample was obtained from the subject. The inventive process determines a first subtype of organ injury based on a first ratio of a plurality of biomarkers. The inventive process also determines a second subtype of a second organ injury based on a second ratio of the plurality of biomarkers in the biological sample. The ratios are illustratively determined by processes described herein or known in the art.

The subject invention illustratively includes a composition for distinguishing the magnitude of a neurological condition in a subject. An inventive composition is either an agent entity or a mixture of multiple agents. In a preferred embodiment a composition is a mixture. The mixture optionally contains a biological sample derived from a subject. The subject is optionally suspected of having a neurological condition. The biological sample in communication with the nervous system of the subject prior to being isolated from the subject. In inventive composition also contains at least two primary agents, preferably antibodies, that specifically and independently bind to at least two biomarkers that may be present in the biological sample. In a preferred embodiment the first primary agent is in antibody that specifically binds GFAP. A second primary agent is preferably an antibody that specifically binds a ubiquitin carboxyl-terminal hydrolase, preferably UCH-L1, or a spectrin breakdown product.

The agents of the inventive composition are optionally immobilized or otherwise in contact with a substrate. The inventive teachings are also preferably labeled with at least one detectable label. In a preferred embodiment the detectable label on each agent is unique and independently detectable in either the same assay chamber or alternate chambers. Optionally a secondary agent specific for detecting or binding to the primary agent is labeled with at least one detectable label. In the nonlimiting example the primary agent is a rabbit derived antibody. A secondary agent is optionally an antibody specific for a rabbit derived primary antibody. Mechanisms of detecting antibody binding to an antigen are well known in the art, and a person of ordinary skill in the art readily envisions numerous methods and agents suitable for detecting antigens or biomarkers in a biological sample.

The invention employs a step of correlating the presence or amount of a biomarker in a biological sample with the severity and/or type of nerve cell (or other biomarker-expressing cell) injury. The amount of biomarker(s) in the biological sample directly relates to severity of nerve tissue injury as a more severe injury damages a greater number of nerve cells which in turn causes a larger amount of biomarker(s) to accumulate in the biological sample (e.g., CSF; serum). Whether a nerve cell injury triggers an apoptotic and/or necrotic type of cell death can also be determined by examining the SBDPs present in the biological sample. Necrotic cell death preferentially activates calpain, whereas apoptotic cell death preferentially activates caspase-3. Because calpain and caspase-3 SBDPs can be distinguished, measurement of these markers indicates the type of cell damage in the subject. For example, necrosis-induced calpain activation results in the production of SBDP150 and SBDP145; apoptosis-induced caspase-3 activation results in the production of SBDP150i and SBDP120; and activation of both pathways results in the production of all four markers. Also, the level of or kinetic extent of UCH-L1 present in a biological sample may optionally distinguish mild injury from a more severe injury. In an illustrative example, severe MCAO (2 h) produces increased UCH-L1 in both CSF and serum relative to mild challenge (30 min) while both produce UCH-L1 levels in excess of uninjured subjects. Moreover, the persistence or kinetic extent of the markers in a biological sample is indicative of the severity of the injury with greater injury indicating increases persistence of GFAP, UCH-L1, or SBDP in the subject that is measured by an inventive process in biological samples taken at several time points following injury.

The results of such a test can help a physician determine whether the administration a particular therapeutic such as calpain and/or caspase inhibitors or muscarinic cholinergic receptor antagonists might be of benefit to a patient. This method may be especially important in detecting age and gender difference in cell death mechanism.

It is appreciated that other reagents such as assay grade water, buffering agents, membranes, assay plates, secondary antibodies, salts, and other ancillary reagents are available from vendors known to those of skill in the art. Illustratively, assay plates are available from Corning, Inc. (Corning, NY) and reagents are available from Sigma-Aldrich Co. (St. Louis, MO).

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, NY, 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian tissue, specifically, analyses of mouse tissue, a person having ordinary skill in the art recognizes that similar techniques and other techniques known in the art readily translate the examples to other mammals such as humans. Reagents illustrated herein are commonly cross reactive between mammalian species or alternative reagents with similar properties are commercially available, and a person of ordinary skill in the art readily understands where such reagents may be obtained. Variations within the concepts of the invention are apparent to those skilled in the art.

Example 1: Materials for Biomarker Analyses

Illustrative reagents used in performing the subject invention include Sodium bicarbonate (Sigma Cat #: C-3041), blocking buffer (Startingblock T20-TBS) (Pierce Cat #: 37543), Tris buffered saline with Tween 20 (TBST; Sigma Cat #: T-9039). Phosphate buffered saline (PBS; Sigma Cat #: P-3813); Tween 20 (Sigma Cat #: P5927); Ultra TMB ELISA (Pierce Cat #: 34028); and Nunc maxisorp ELISA plates (Fisher). Monoclonal and polyclonal GFAP and UCH-L1 antibodies are made in-house or are obtained from Santa Cruz Biotechnology, Santa Cruz, CA Antibodies directed to α-II spectrin and breakdown products as well as to MAP2 are available from Santa Cruz Biotechnology, Santa Cruz, CA Labels for antibodies of numerous subtypes are available from Invitrogen, Corp., Carlsbad, CA Protein concentrations in biological samples are determined using bicinchoninic acid microprotein assays (Pierce Inc., Rockford, IL, USA) with albumin standards. All other necessary reagents and materials are known to those of skill in the art and are readily ascertainable.

Example 2: Biomarker Assay Development

Anti-biomarker specific rabbit polyclonal antibody and monoclonal antibodies are produced in the laboratory. To determine reactivity specificity of the antibodies to detect a target biomarker a known quantity of isolated or partially isolated biomarker is analyzed or a tissue panel is probed by western blot. An indirect ELISA is used with the recombinant biomarker protein attached to the ELISA plate to determine optimal concentration of the antibodies used in the assay. Microplate wells are coated with rabbit polyclonal anti-human biomarker antibody. After determining the concentration of rabbit anti-human biomarker antibody for a maximum signal, the lower detection limit of the indirect ELISA for each antibody is determined. An appropriate diluted sample is incubated with a rabbit polyclonal antihuman biomarker antibody for 2 hours and then washed. Biotin labeled monoclonal anti-human biomarker antibody is then added and incubated with captured biomarker. After thorough wash, streptavidin horseradish peroxidase conjugate is added. After 1 hour incubation and the last washing step, the remaining conjugate is allowed to react with substrate of hydrogen peroxide tetramethyl benzandine. The reaction is stopped by addition of the acidic solution and absorbance of the resulting yellow reaction product is measured at 450 nanometers. The absorbance is proportional to the concentration of the biomarker. A standard curve is constructed by plotting absorbance values as a function of biomarker concentration using calibrator samples and concentrations of unknown samples are determined using the standard curve.

Example 3: In Vivo Model of TBI Injury Model

A controlled cortical impact (CCI) device is used to model TBI on rats as previously described (Pike et al, 1998). Adult male (280-300 g) Sprague-Dawley rats (Harlan: Indianapolis, IN) are anesthetized with 4% isoflurane in a carrier gas of 1:1 $O_2$/N20 (4 min.) and maintained in 2.5% isoflurane in the same carrier gas. Core body temperature is monitored continuously by a rectal thermistor probe and maintained at 37±1° C. by placing an adjustable temperature controlled heating pad beneath the rats. Animals are mounted in a stereotactic frame in a prone position and secured by ear and incisor bars. Following a midline cranial incision and reflection of the soft tissues, a unilateral (ipsilateral to site of impact) craniotomy (7 mm diameter) is performed adjacent to the central suture, midway between bregma and lambda. The dura mater is kept intact over the cortex. Brain trauma is produced by impacting the right (ipsilateral) cortex with a 5 mm diameter aluminum impactor tip (housed in a pneumatic cylinder) at a velocity of 3.5 m/s with a 1.6 mm compression and 150 ms dwell time. Sham-injured control animals are subjected to identical surgical procedures but do not receive the impact injury. Appropriate pre- and post-injury management is preformed to insure compliance with guidelines set forth by the University of Florida Institutional Animal Care and Use Committee and the National Institutes of Health guidelines detailed in the Guide for the Care and Use of Laboratory Animals. In addition, research is conducted in compliance with the Animal Welfare Act and other federal statutes and regulations relating to animals and experiments involving animals and adhered to principles stated in the "Guide for the Care and Use of Laboratory Animals, NRC Publication, 1996 edition."

Example 4: Middle Cerebral Artery Occlusion (MCAO) Injury Model

Rats are incubated under isoflurane anesthesia (5% isoflurane via induction chamber followed by 2% isoflurane via nose cone), the right common carotid artery (CCA) of the rat is exposed at the external and internal carotid artery (ECA and ICA) bifurcation level with a midline neck incision. The ICA is followed rostrally to the pterygopalatine branch and the ECA is ligated and cut at its lingual and maxillary branches. A 3-0 nylon suture is then introduced into the ICA via an incision on the ECA stump (the suture's path was visually monitored through the vessel wall) and advanced through the carotid canal approximately 20 mm from the carotid bifurcation until it becomes lodged in the narrowing of the anterior cerebral artery blocking the origin of the middle cerebral artery. The skin incision is then closed and the endovascular suture left in place for 30 minutes or 2 hours. Afterwards the rat is briefly reanesthetized and the suture filament is retracted to allow reperfusion. For sham MCAO surgeries, the same procedure is followed, but the filament is advanced only 10 mm beyond the internal-external carotid bifurcation and is left in place until the rat is sacrificed. During all surgical procedures, animals are maintained at 37±1° C. by a homeothermic heating blanket (Harvard Apparatus, Holliston, MA, U.S.A.). It is important to note that at the conclusion of each experiment, if the rat brains show pathologic evidence of subarachnoid hemorrhage upon necropsy they are excluded from the study. Appropriate pre- and post-injury management is preformed to insure compliance with all animal care and use guidelines.

Example 5: Tissue and Sample Preparation

At the appropriate time points (2, 6, 24 hours and 2, 3, 5 days) after injury, animals are anesthetized and immediately sacrificed by decapitation. Brains are quickly removed, rinsed with ice cold PBS and halved. The right hemisphere (cerebrocortex around the impact area and hippocampus) is rapidly dissected, rinsed in ice cold PBS, snap-frozen in liquid nitrogen, and stored at −80° C. until used. For immunohistochemistry, brains are quick frozen in dry ice slurry, sectioned via cryostat (20 µm) onto SUPERFROST PLUS GOLD® (Fisher Scientific) slides, and then stored at −80° C. until used. For the left hemisphere, the same tissue as the right side is collected. For Western blot analysis, the brain samples are pulverized with a small mortar and pestle set over dry ice to a fine powder. The pulverized brain tissue powder is then lysed for 90 min at 4° C. in a buffer of 50 mM Tris (pH 7.4), 5 mM EDTA, 1% (v/v) Triton X-100, 1 mM DTT, 1× protease inhibitor cocktail (Roche Biochemicals). The brain lysates are then centrifuged at 15,000×g for 5 min at 4° C. to clear and remove insoluble debris, snap-frozen, and stored at −80° C. until used.

For gel electrophoresis and electroblotting, cleared CSF samples (7 µl) are prepared for sodium dodecyl sulfate-polyacrylamide gel electrophoresis (SDS-PAGE) with a 2× loading buffer containing 0.25 M Tris (pH 6.8), 0.2 M DTT, 8% SDS, 0.02% bromophenol blue, and 20% glycerol in distilled H2O. Twenty micrograms (20 µg) of protein per lane are routinely resolved by SDS-PAGE on 10-20% Tris/glycine gels (Invitrogen, Cat #EC61352) at 130 V for 2 hours. Following electrophoresis, separated proteins are laterally transferred to polyvinylidene fluoride (PVDF) membranes in a transfer buffer containing 39 mM glycine, 48 mM Tris-HCl (pH 8.3), and 5% methanol at a constant voltage of 20 V for 2 hours at ambient temperature in a semi-dry transfer unit (Bio-Rad). After electro-transfer, the membranes are blocked for 1 hour at ambient temperature in 5% non-fat milk in TBS and 0.05% Tween-2 (TBST) then are incubated with the primary polyclonal UCH-L1 antibody in TBST with 5% non-fat milk at 1:2000 dilution as recommended by the manufacturer at 4° C. overnight. This is followed by three washes with TBST, a 2 hour incubation at ambient temperature with a biotinylated linked secondary antibody (Amersham, Cat #RPN1177v1), and a 30 min incubation with Streptavidin-conjugated alkaline phosphatase (BCIP/NBT reagent: KPL, Cat #50-81-08). Molecular weights of intact biomarker proteins are assessed using rainbow colored molecular weight standards (Amersham, Cat #RPN800V). Semi-quantitative evaluation of intact GFAP, UCH-L1, or SBDP protein levels is performed via computer-assisted densitometric scanning (Epson XL3500 scanner) and image analysis with ImageJ software (NIH).

Example 6: UCH-L1 is Increased in CSF Following MCAO Challenge

Subjects are subjected to MCAO challenge and CSF samples analyzed by quantitative western blotting. UCH-L1 protein is readily detectable after injury at statically significant levels above the amounts of UCH-L1 in sham treated samples (FIGS. 1A, B). These UCH-L1 levels are transiently elevated (at 6 h) after mild ischemia (30 min MCAO)

followed by reperfusion, while levels are sustained from 6 to 72 h after a more severe (2 h MCAO) ischemia (FIGS. 1A, B).

Example 7: ELISA Readily Identifies UCH-L1 Levels in Both CSF and Serum

ELISA is used to more rapidly and readily detect and quantitate UCH-L1 in biological samples. For a UCH-L1 sandwich ELISA (swELISA), 96-well plates are coated with 100 µl/well capture antibody (500 ng/well purified rabbit anti-UCH-L1, made in-house by conventional techniques) in 0.1 M sodium bicarbonate, pH 9.2. Plates are incubated overnight at 4° C., emptied and 300 µl/well blocking buffer (Startingblock T20-TBS) is added and incubated for 30 min at ambient temperature with gentle shaking. This is followed by either the addition of the antigen standard (recombinant UCH-L1) for standard curve (0.05-50 ng/well) or samples (3-10 µl CSF) in sample diluent (total volume 100 µl/well). The plate is incubated for 2 hours at room temperature, then washed with automatic plate washer (5×300 µl/well with wash buffer, TBST). Detection antibody mouse anti-UCH-L1-HRP conjugated (made in-house, 50 µg/ml) in blocking buffer is then added to wells at 100 µL/well and incubated for 1.5 h at room temperature, followed by washing. If amplification is needed, biotinyl-tyramide solution (Perkin Elmer Elast Amplification Kit) is added for 15 min at room temperature, washed then followed by 100 µl/well streptavidin-HRP (1:500) in PBS with 0.02% Tween-20 and 1% BSA for 30 min and then followed by washing. Lastly, the wells are developed with 100 µL/well TMB substrate solution (Ultra-TMB ELISA, Pierce #34028) with incubation times of 5-30 minutes. The signal is read at 652 nm with a 96-well spectrophotometer (Molecular Device Spectramax 190).

Figure 2:
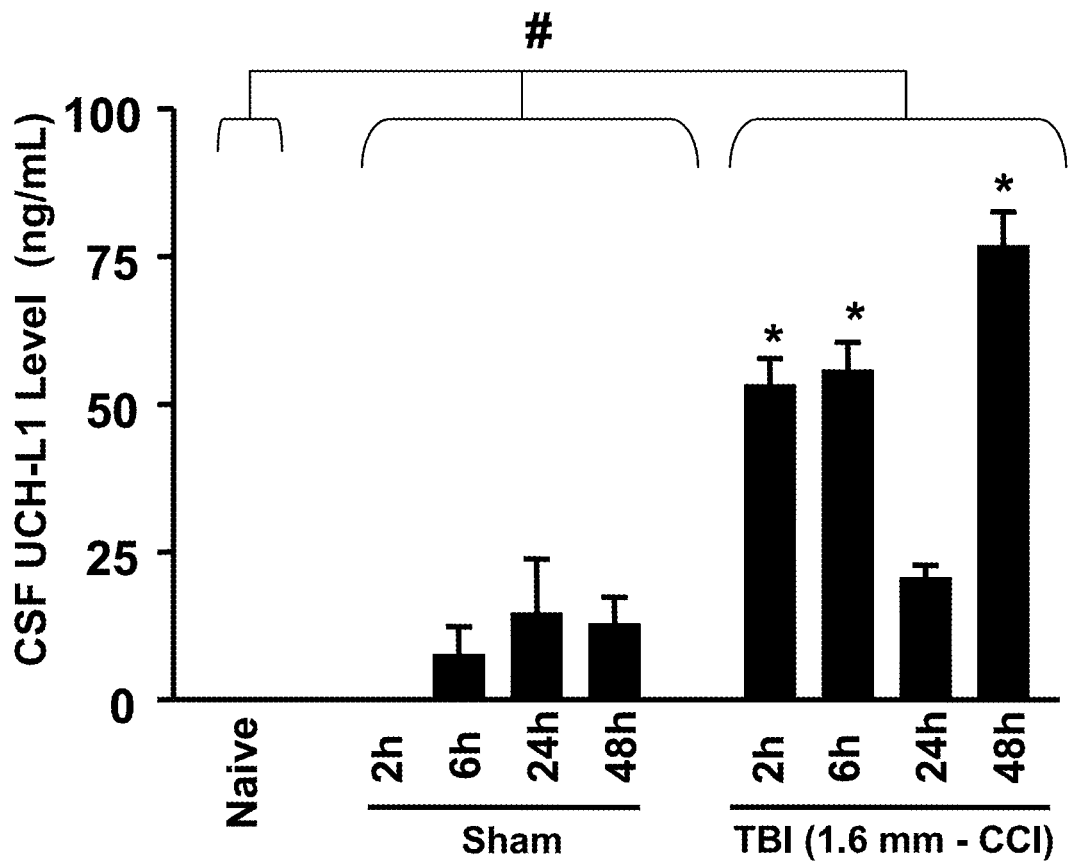
FIG. 2 represents UCH-L1 levels in CSF in sham and CCI treated subjects.

UCH-L1 levels of the TBI group (percussive injury) are significantly higher than the sham controls (p<0.01, ANOVA analysis) and the naïve controls as measured by a swELISA demonstrating that UCH-L1 is elevated early in CSF (2 h after injury) then declines at around 24 h after injury before rising again 48 h after injury (FIG. 2).

Figure 3:
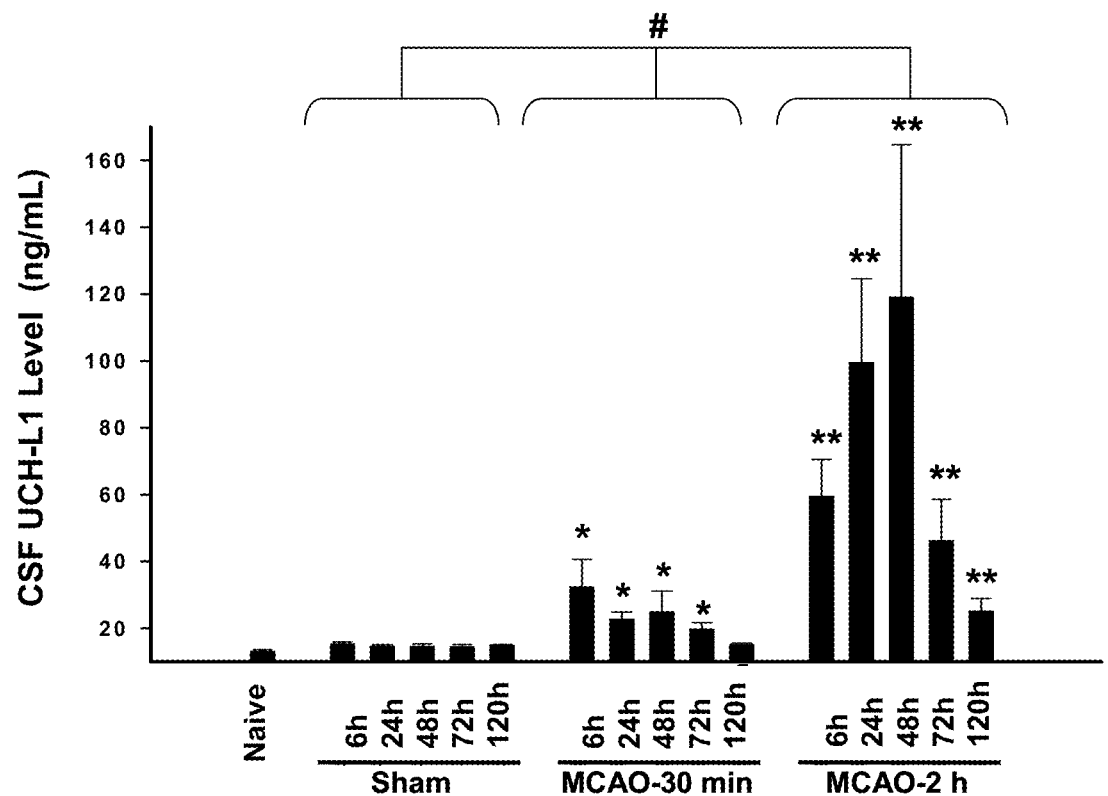
FIG. 3 represents UCH-L1 levels in CSF following sham, mild MCAO challenge, and severe MCAO challenge.

Following MCAO challenge the magnitude of UCH-L1 in CSF is dramatically increased with severe (2 h) challenge relative to a more mild challenge (30 min). (FIG. 3) The more severe 2 h MCAO group UCH-L1 protein levels are 2-5 fold higher than 30 min MCAO (p<0.01, ANOVA analysis). UCH-L1 protein levels for shams are virtually indistinguishable from naïve controls.

Figure 4:
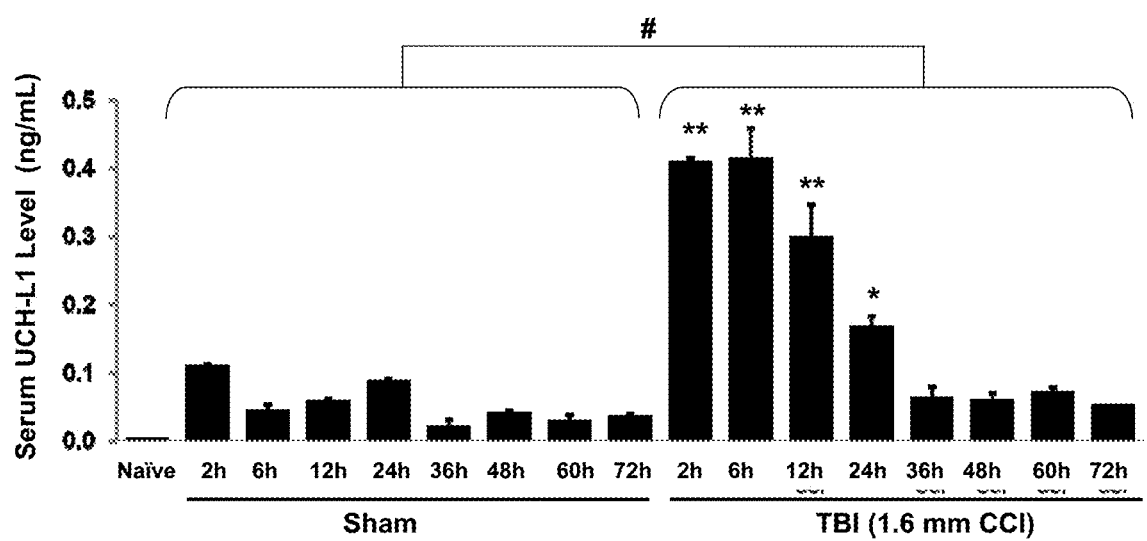
FIG. 4 represents UCH-L1 levels in serum following sham or CCI at various timepoints.
Figure 5:
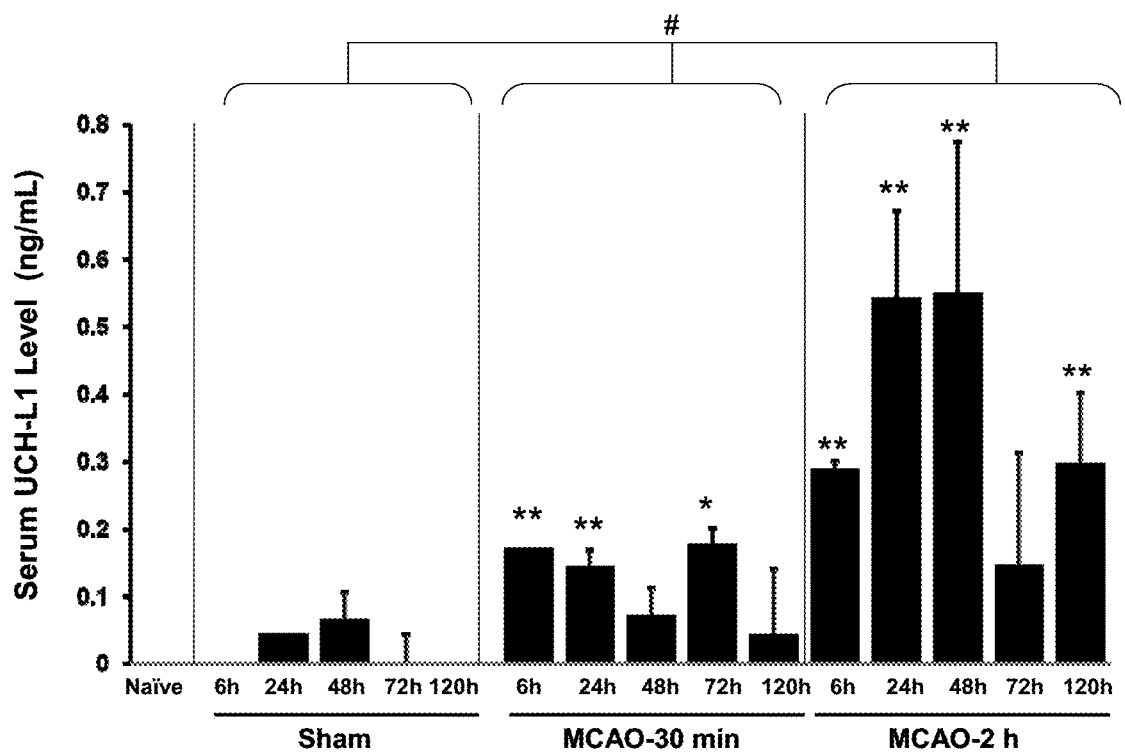
FIG. 5 represents UCH-L1 levels in serum following sham, mild MCAO challenge, and severe MCAO challenge.

Similar results are obtained for UCH-L1 in serum. Blood (3-4 ml) is collected at the end of each experimental period directly from the heart using syringe equipped with 21 gage needle placed in a polypropylene tube and allowed to stand for 45 min to 1 hour at room temperature to form clot. Tubes are centrifuged for 20 min at 3,000×g and the serum removed and analyzed by ELISA (FIGS. 4, 5).

UCH-L1 levels of the TBI group are significantly higher than the sham group (p<0.001, ANOVA analysis) and for each time point tested 2 h through 24 h respective to the same sham time points (p<0.005, Student's T-test). UCH-L1 is significantly elevated after injury as early as 2 h in serum. Severe MCAO challenge produces increased serum UCH-L1 relative to mild challenge. Both mild and severe challenge are statistically higher than sham treated animals indicating that serum detection of UCH-L1 is a robust diagnostic and the levels are able to sufficiently distinguish mild from severe injury.

Example 8: Analysis of Spectrin Breakdown Products

Figure 6:
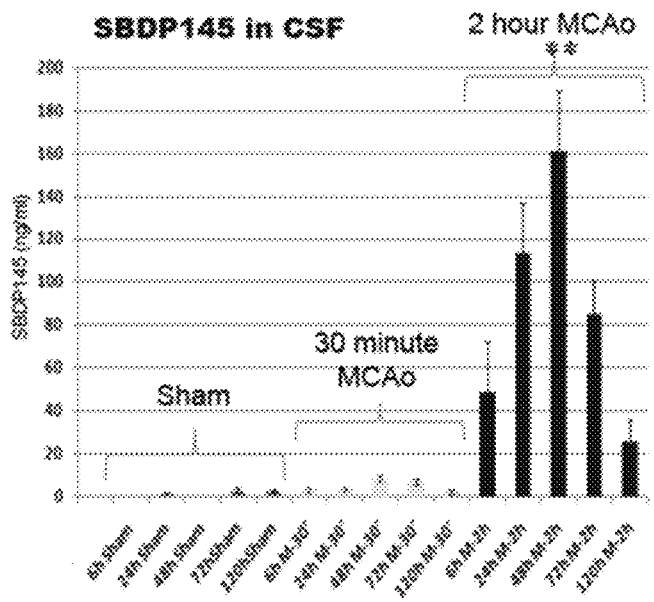
FIG. 6 represents SBDP145 levels in CSF and serum following sham, mild MCAO challenge, and severe MCAO challenge.
Figure 6:
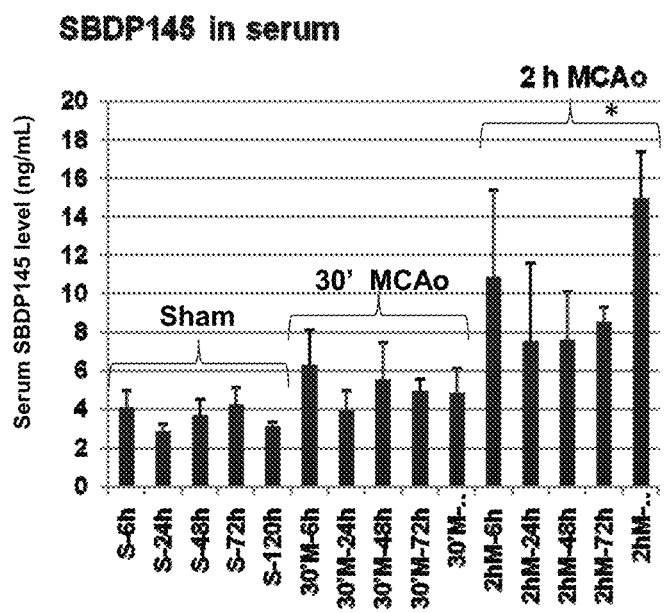
Figure 7:
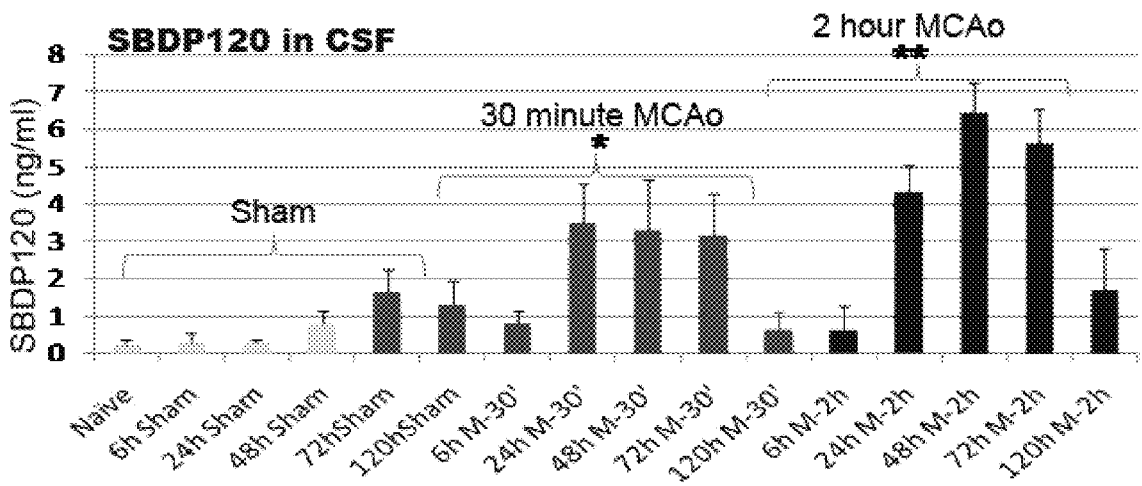
FIG. 7 represents SBDP120 levels in CSF and serum following sham, mild MCAO challenge, and severe MCAO challenge.
Figure 7:
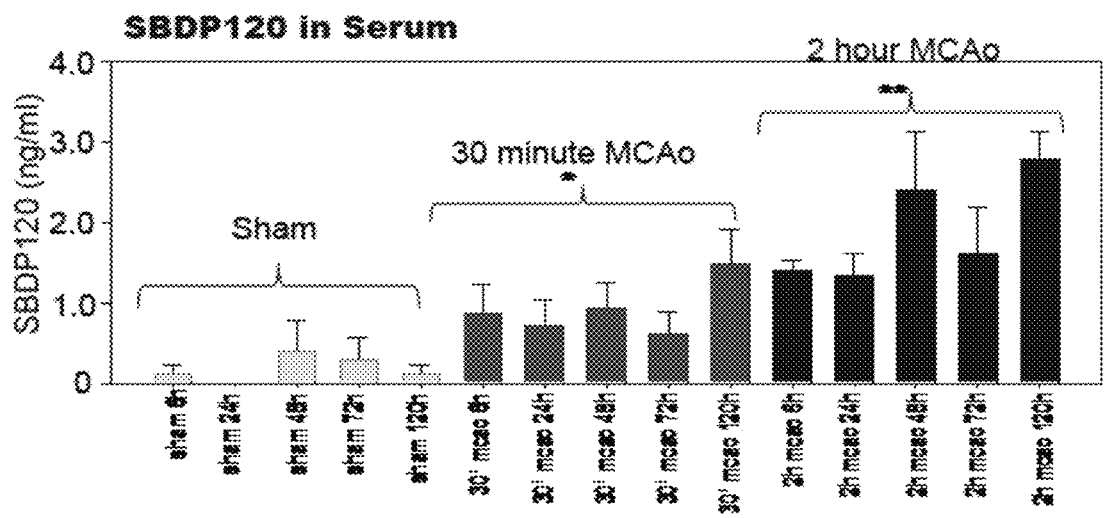

Spectrin breakdown products are analyzed following rat MCAO challenge by procedures similar to those described in U.S. Pat. No. 7,291,710, the contents of which are incorporated herein by reference. FIG. 6 demonstrates that levels of SBDP145 in both serum and CSF are significantly (p<0.05) increased at all time points studied following severe (2 hr) MCAO challenge relative to mild (30 min) challenge. Similarly, SBDP120 demonstrates significant elevations following severe MCAO challenge between 24 and 72 hours after injury in CSF (FIG. 7). However, levels of SBDP120 in serum are increased following severe challenge relative to mild challenge at all time points between 2 and 120 hours. In both CSF and Serum both mild and severe MCAO challenge produces increased SPBP120 and 140 relative to sham treated subjects.

Example 9: Analysis of MAP2

Figure 8:
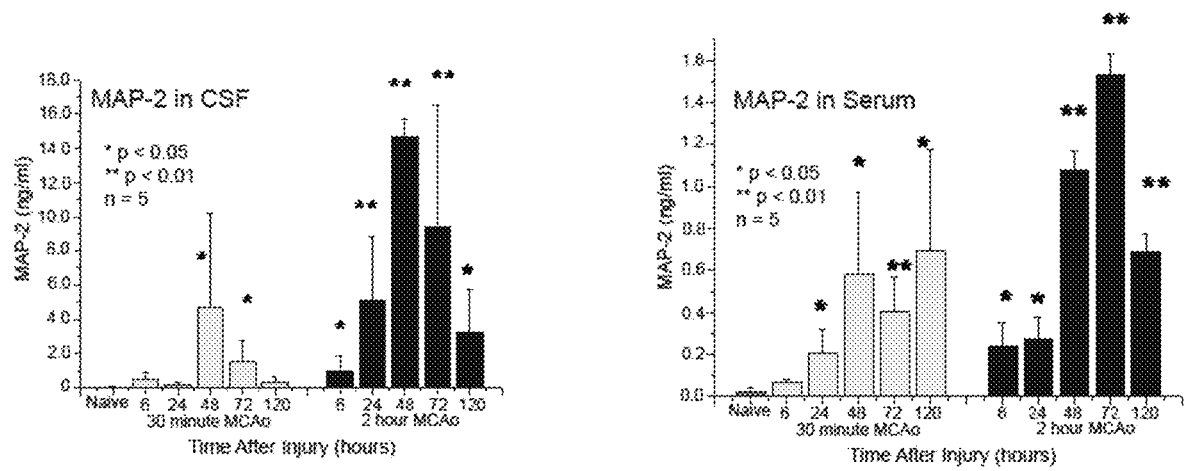
FIG. 8 represents MAP2 elevation in CSF and serum following sham, mild MCAO challenge, and severe MCAO challenge.

Microtubule Associated Protein 2 (MAP2) is assayed as a biomarker in both CSF and serum following mild (30 min) and severe (2 hr) MCAO challenge in subjects by ELISA or western blotting essentially as described herein. Antibodies to MAP2 (MAP-2 (E-12)) are obtained from Santa Cruz Biotechnology, Santa Cruz, CA These antibodies are suitable for both ELISA and western blotting procedures and are crossreactive to murine and human MAP2. Levels of MAP2 are significantly (p<0.05) increased in subjects following mild MCAO challenge relative to naive animals in both CSF and serum (FIG. 8). Similar to UCH-L1 and SBDPs, severe challenge (2 hr) produces much higher levels of MAP2 in both samples than mild challenge (30 min).

Example 10: Severe Traumatic Brain Injury Study

A study was conducted that included 46 human subjects suffering severe traumatic brain injury. Each of these subjects is characterized by being over age 18, having a GCS of less than or equal to 8 and required ventriculostomy and neuromonitoring as part of routine care. A control group A, synonymously detailed as CSF controls, included 10 individuals also being over the age of 18 or older and no injuries. Samples are obtained during spinal anesthesia for routine surgical procedures or access to CSF associated with treatment of hydrocephalus or meningitis. A control group B, synonymously described as normal controls, totaled 64 individuals, each age 18 or older and experiencing multiple injuries without brain injury. Further details with respect to the demographics of the study are provided in Table 1.

TABLE 1

Subject Demographics for Severe Traumatic Brain Injury Study

|   |   | TBI | CSF Controls | Normal Controls |
|---|---|---|---|---|
| Number |   | 46 | 10 | 64 |
|   | Males | 34 (73.9%) | 29 (65.9%) | 26 (40.6%) |
|   | Females | 12 (26.1%) | 15 (34.1%) | 38 (59.4%) |
| Age: | Average | 50.2 | 58.2 1, 2 | 30.09 2, 3 |
|   | Std Dev | 19.54 | 20.52 | 15.42 |
|   | Minimum | 19 | 23 | 18 |
|   | Maximum | 88 | 82 | 74 |

TABLE 1-continued

Subject Demographics for Severe Traumatic Brain Injury Study

|  |  | TBI | CSF Controls | Normal Controls |
|---|---|---|---|---|
| Race: | Caucasian |  |  |  |
|  | Black | 45 | 38 (86.4%) | 52 (81.2%) |
|  | Asian | 1 | 6 (13.6) | 4 (6.3%) |
|  | Other |  |  | 7 (10.9%) |
|  |  |  |  | 1 (1.6%) |
| GCS in Emergency Department |  |  |  |  |
|  | Average | 5.3 |  |  |
|  | Std Dev | 1.9 |  |  |

Figure 9:
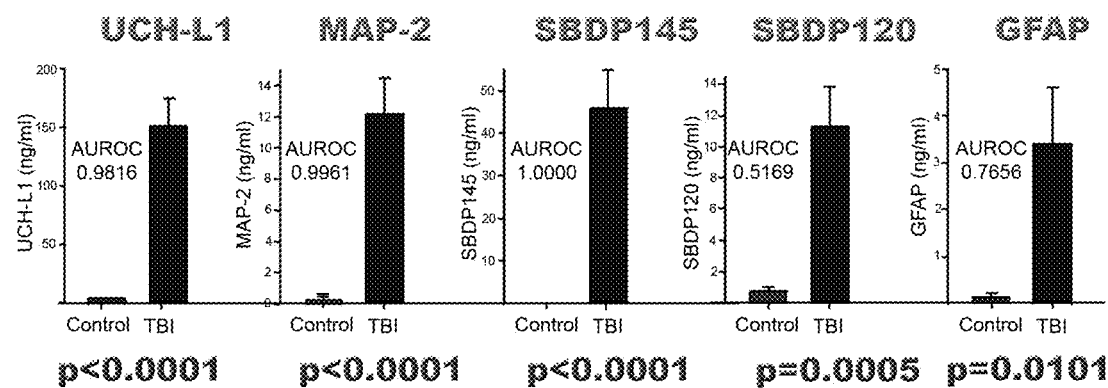
FIG. 9 are bar graphs of GFAP and other biomarkers for human control and severe TBI subjects from CSF samples.
Figure 10:
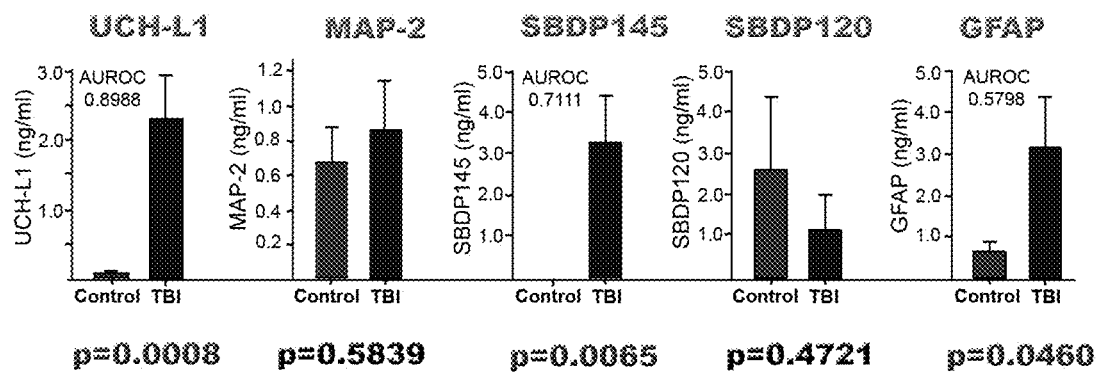
FIG. 10 are bar graphs of GFAP and other biomarkers for human control and severe TBI subjects of FIG. 1 from serum samples.
Figure 11:
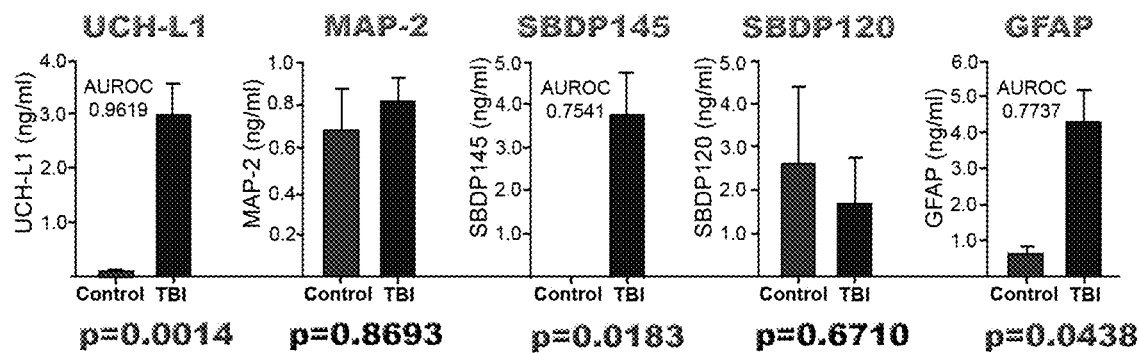
FIG. 11 are bar graphs of GFAP and other biomarkers for human control and severe TBI subjects summarizing the data of FIGS. 9 and 10.

The level of biomarkers found in the first available CSF and serum samples obtained in the study are provided in FIGS. 9 and 10, respectively. The average first CSF sample collected as detailed in FIG. 9 was 11.2 hours while the average time for collection of a serum sample subsequent to injury event as per FIG. 10 is 10.1 hours. The quantity of each of the biomarkers of UCH-L1, MAP2, SBDP145, SBDP120, and GFAP are provided for each sample for the cohort of traumatic brain injury sufferers as compared to a control group. The diagnostic utility of the various biomarkers within the first 12 hours subsequent to injury based on a compilation of CSF and serum data is provided in FIG. 11 and indicates in particular the value of GFAP as well as that of additional markers UCH-L1 and the spectrin breakdown products. Elevated levels of UCH-L1 are indicative of the compromise of neuronal cell body damage while an increase in SPDP145 with a corresponding decrease in SBDP120 is suggestive of acute axonal necrosis.

Figure 12:
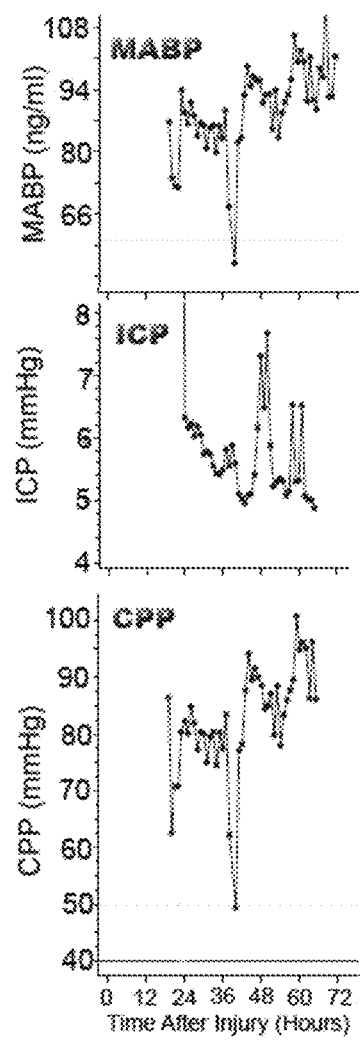
FIG. 12 are plots of arterial blood pressure (MABP), intracranial pressure (ICP) and cerebral profusion pressure (CPP) for a single human subject of traumatic brain injury as a function of time.
Figure 13:
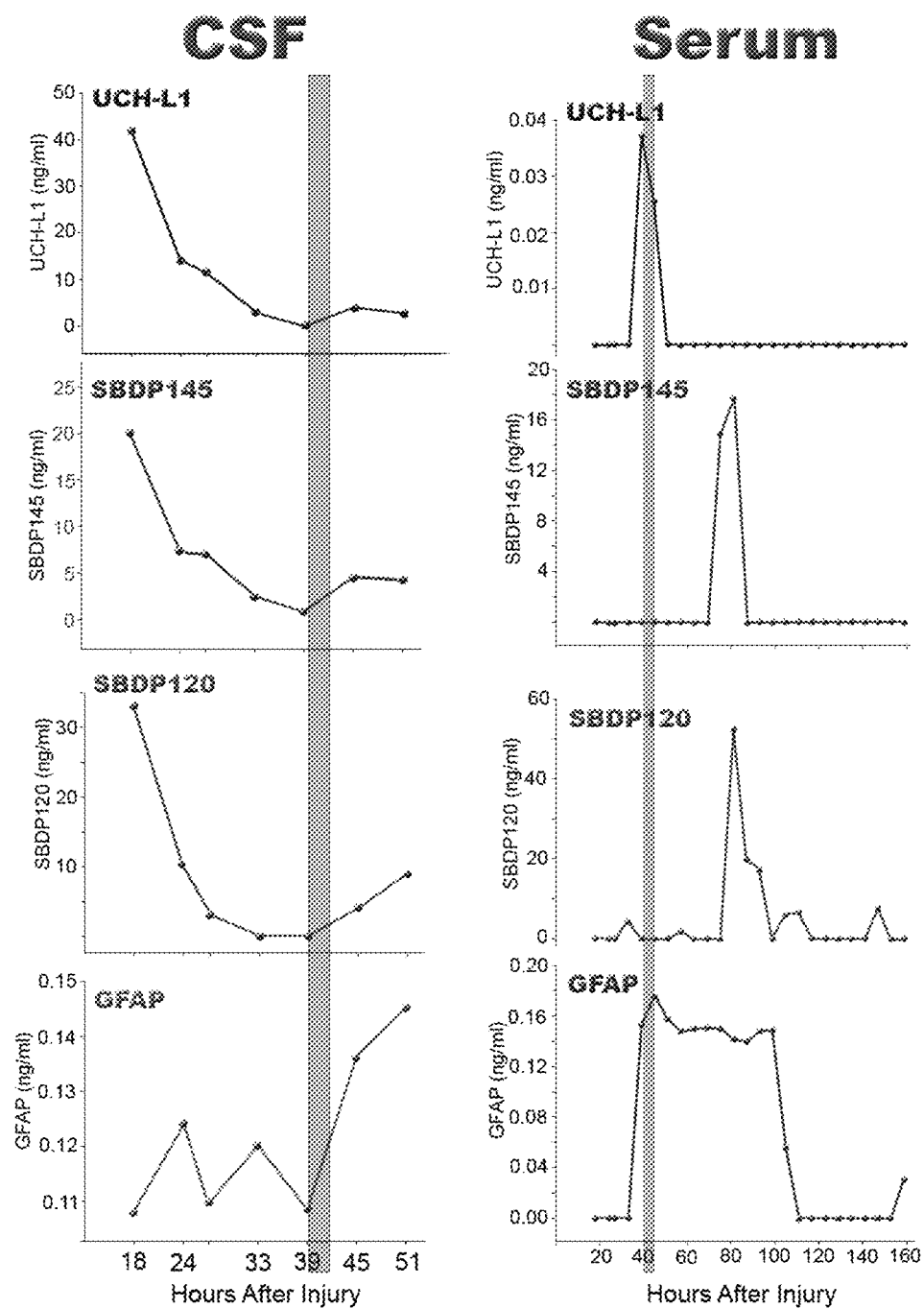
FIG. 13 are plots of inventive biomarkers from CSF and serum samples from the single human subject of traumatic brain injury of FIG. 12 as a function of time.

One subject from the traumatic brain injury cohort was a 52 year old Caucasian woman who had been involved in a motorcycle accident while not wearing a helmet. Upon admission to an emergency room her GCS was 3 and during the first 24 hours subsequent to trauma her best GCS was 8. After 10 days her GCS was 11. CT scanning revealed SAH and facial fractures with a Marshall score of 11 and a Rotterdam score of 2. Ventriculostomy was removed after 5 years and an overall good outcome was obtained. Arterial blood pressure (MABP), intracranial pressure (ICP) and cerebral profusion pressure (CPP) for this sufferer of traumatic brain injury as a function of time is depicted in FIG. 12. A possible secondary insult is noted at approximately 40 hours subsequent to the injury as noted by a drop in MABP and CPP. The changes in concentration of inventive biomarkers per CSF and serum samples from this individual are noted in FIG. 13. These results include a sharp increase in GFAP in both the CSF and serum as well as the changes in the other biomarkers depicted in FIG. 13 and provide important clinical information as to the nature of the injury and the types of cells involved, as well as modes of cell death associated with the spectrin breakdown products.

Figure 14:
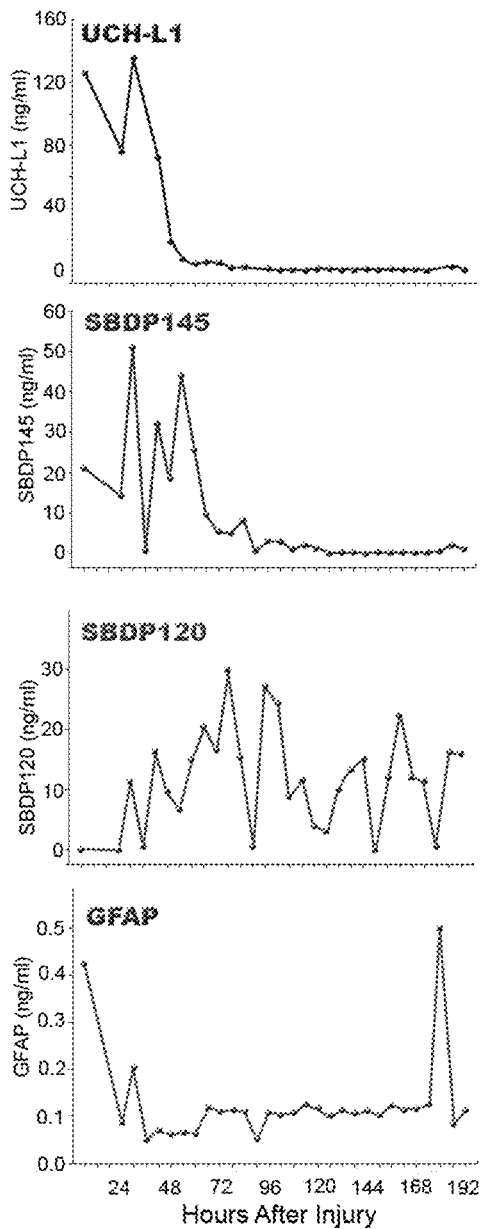
FIG. 14 are plots of inventive biomarkers from CSF and serum samples from another individual human subject of traumatic brain injury as a function of time.
Figure 14:
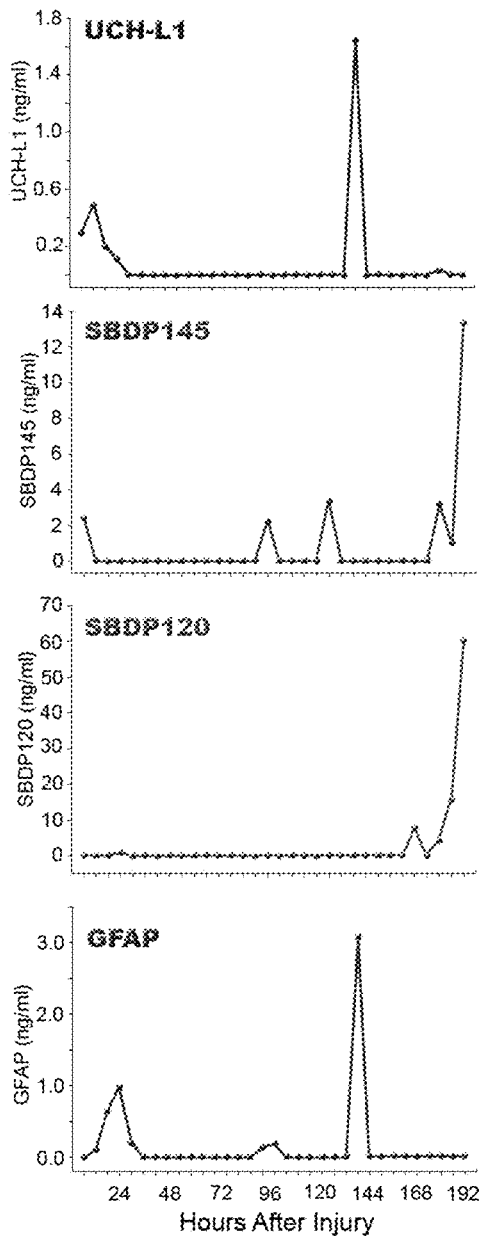
Figure 15:
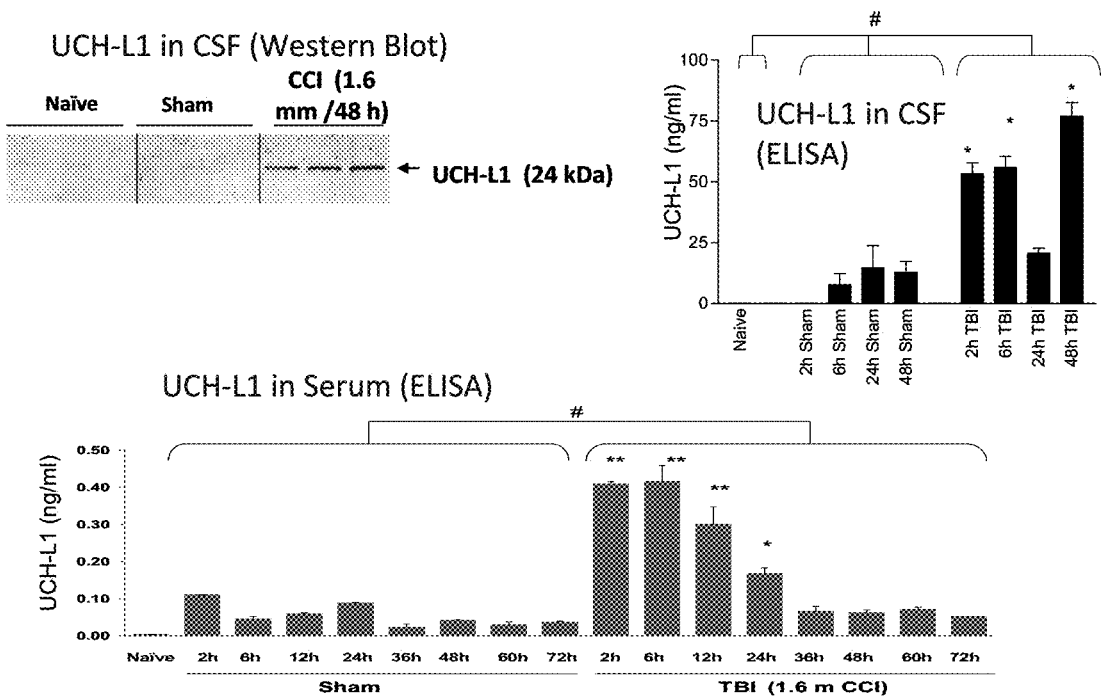
FIG. 15 are plots of UCH-L1 amounts being present in CSF and serum post severe traumatic brain injury in a mouse subject.

Another individual of the severe traumatic brain injury cohort included a 51 year old Caucasian woman who suffered a crush injury associated with a horse falling on the individual. GCS on admission to emergency room was 3 with imaging analysis initially being unremarkable with minor cortical and subcortical contusions. MRI on day 5 revealed significant contusions in posterior fossa. The Marshall scale at that point was indicated to be 11 with a Rotterdam scale score of 3. The subject deteriorated and care was withdrawn 10 days after injury. The CSF and serum values for this individual during a period of time are provided in FIG. 14.

Based on the sandwich ELISA testing, GFAP values as a function of time are noted to be markedly elevated relative to normal controls (control group B) as a function of time.

The concentration of spectrin breakdown products, MAP2 and UCH-L1 as a function of time subsequent to traumatic brain injury has been reported elsewhere as exemplified in U.S. Pat. Nos. 7,291,710 and 7,396,654 each of which is incorporated herein by reference.

An analysis was performed to evaluate the ability of biomarkers measured in serum to predict TBI outcome, specifically GCS. Stepwise regression analysis was the statistical method used to evaluate each of the biomarkers as an independent predictive factor, along with the demographic factors of age and gender, and also interactions between pairs of factors. Interactions determine important predictive potential between related factors, such as when the relationship between a biomarker and outcome may be different for men and women, such a relationship would be defined as a gender by biomarker interaction.

The resulting analysis identified biomarkers UCH-L1, MAP2, and GFAP as being statistically significant predictors of GCS (Table 2, 3). Furthermore, GFAP was shown to have improved predictability when evaluated in interaction with UCH-L1 and gender (Table 4, 5).

TABLE 2

Stepwise Regression Analysis 1-Cohort includes:
All Subjects >= 18 Years Old

Summary of Stepwise Selection-48 Subjects

| Variable Step Entered | Parameter Estimate | Model R-Square | F Value | p-value |
|---|---|---|---|---|
| Intercept | 13.02579 |  |  |  |
| 2 SEXCD | −2.99242 | 0.1580 | 7.29 | 0.0098 |
| 1 CSF_UCH_L1 | −0.01164 | 0.2519 | 11.54 | 0.0015 |
| 3 Serum_MAP_2 | 0.96055 | 0.3226 | 4.59 | 0.0377 |

TABLE 3

Stepwise Regression Analysis 2-Cohort includes:
TBI Subjects >= 18 Years Old

Summary of Stepwise Selection-39 Subjects

| Variable Step Entered | Parameter Estimate | Model R-Square | F Value | p-value |
|---|---|---|---|---|
| Intercept | 5.73685 |  |  |  |
| 1 Serum_UCH_L1 | −0.30025 | 0.0821 | 8.82 | 0.0053 |
| 2 Serum_GFAP | 0.12083 | 0.1973 | 5.16 | 0.0291 |

TABLE 4

Stepwise Regression Analysis 1-Cohort includes:
TBI and A Subjects >= 18 Years Old Summary of Stepwise Selection-57 Subjects

| Variable Step Entered | Parameter Estimate | Model R-Square | F Value | p-value |
|---|---|---|---|---|
| Intercept | 8.04382 |  |  |  |
| 1 Serum_UCH_L | −0.92556 | 0.1126 | 12.90 | 0.0007 |
| 2 Serum_MAP_2 | 1.07573 | 0.2061 | 5.79 | 0.0197 |
| 3 Serum_UCH-L1 + Serum_GFAP | 0.01643 | 0.2663 | 4.35 | 0.0419 |

TABLE 5

Stepwise Regression Analysis 2-Cohort includes:
TBI Subjects >= 18 Years Old

Summary of Stepwise Selection-44 Subjects

| Variable Step Entered | Parameter Estimate | Model R-Square | F Value | p-value |
|---|---|---|---|---|
| Intercept | 5.50479 | | | |
| 1 Serum_UCH_L1 | −0.36311 | 0.0737 | 11.95 | 0.0013 |
| 2 SEX_Serum_GFAP | 0.05922 | 0.1840 | 5.09 | 0.0296 |
| 3 Serum_MAP_2 | 0.63072 | 0.2336 | 2.59 | 0.1157 |

Example 11

The study of Example 10 was repeated with a moderate traumatic brain injury cohort characterized by GCS scores of between 9 and 11, as well as a mild traumatic brain injury cohort characterized by GCS scores of 12-15. Blood samples were obtained from each patient on arrival to the emergency department of a hospital within 2 hours of injury and measured by ELISA for levels of GFAP in nanograms per milliliter. The results were compared to those of a control group who had not experienced any form of injury. Secondary outcomes included the presence of intracranial lesions in head CT scans.

Over 3 months 53 patients were enrolled: 35 with GCS 13-15, 4 with GCS 9-12 and 14 controls. The mean age was 37 years (range 18-69) and 66% were male. The mean GFAP serum level was 0 in control patients, 0.107 (0.012) in patients with GCS 13-15 and 0.366 (0.126) in GCS 9-12 (P<0.001). The difference between GCS 13-15 and controls was significant at P<0.001. In patients with intracranial lesions on CT GFAP levels were 0.234 (0.055) compared to 0.085 (0.003) in patients without lesions (P<0.001). There is a significant increase in GFAP in serum following a MTBI compared to uninjured controls in both the mild and moderate groups. GFAP was also significantly associated with the presence of intracranial lesions on CT.

Figure 16:
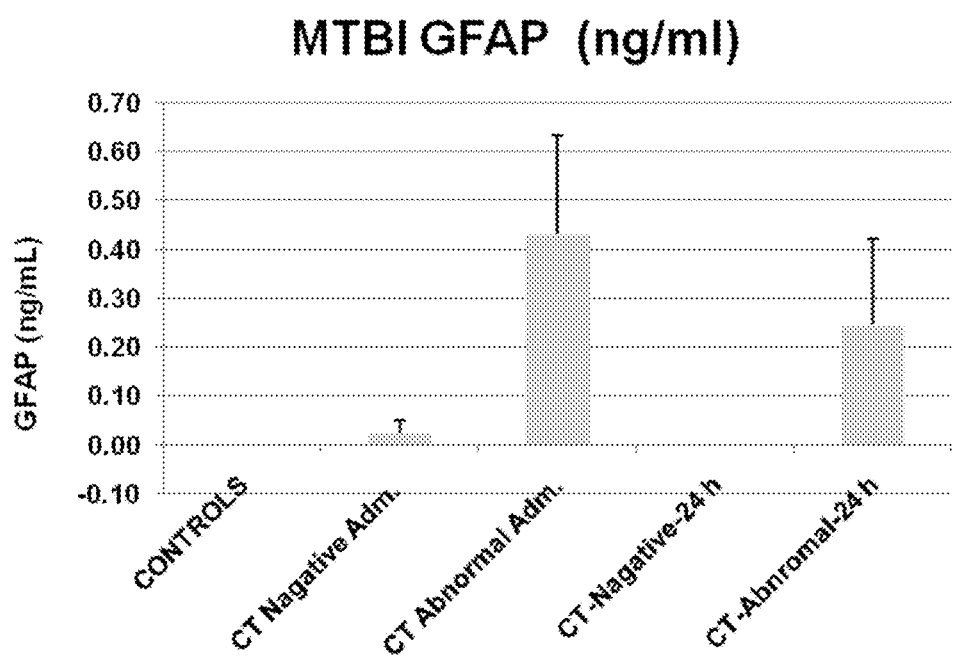
FIG. 16 are bar graphs of GFAP concentration for controls, as well as individuals in the mild/moderate traumatic brain injury cohort as a function of CT scan results upon admission and 24 hours thereafter.
Figure 17:
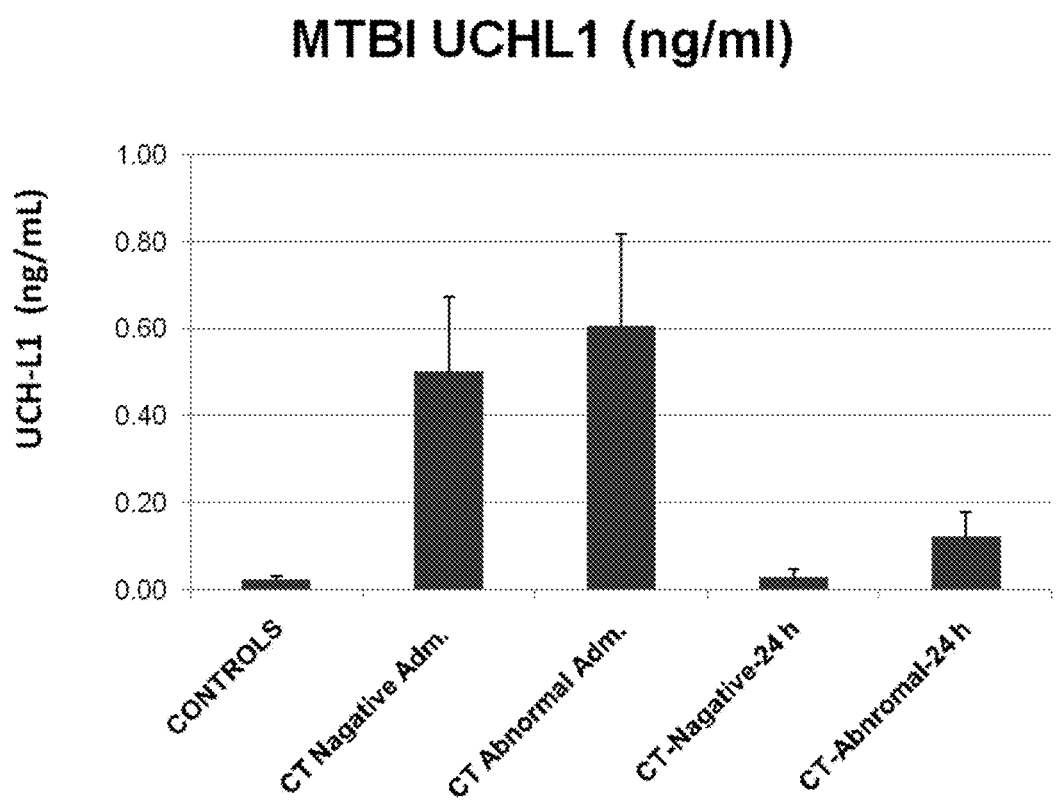
FIG. 17 are bar graphs of parallel assays for UCH-L1 biomarker from the samples used for FIG. 16.
Figure 18:
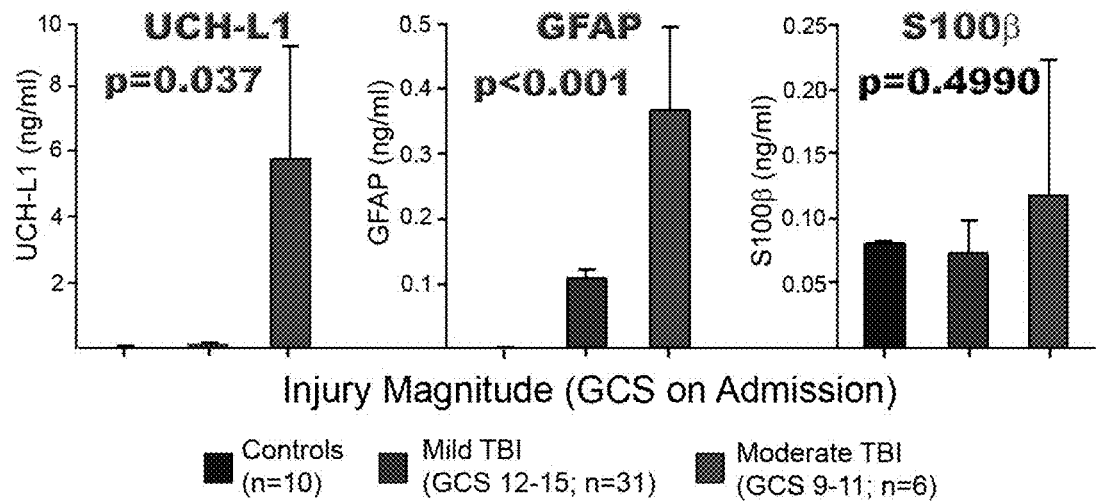
FIG. 18 are bar graphs showing the concentration of UCH-L1 and GFAP as well as a biomarker not selected for diagnosis of neurological condition, S100 beta, provided as a function of injury magnitude between control, mild, and moderate traumatic brain injury.
Figure 19:
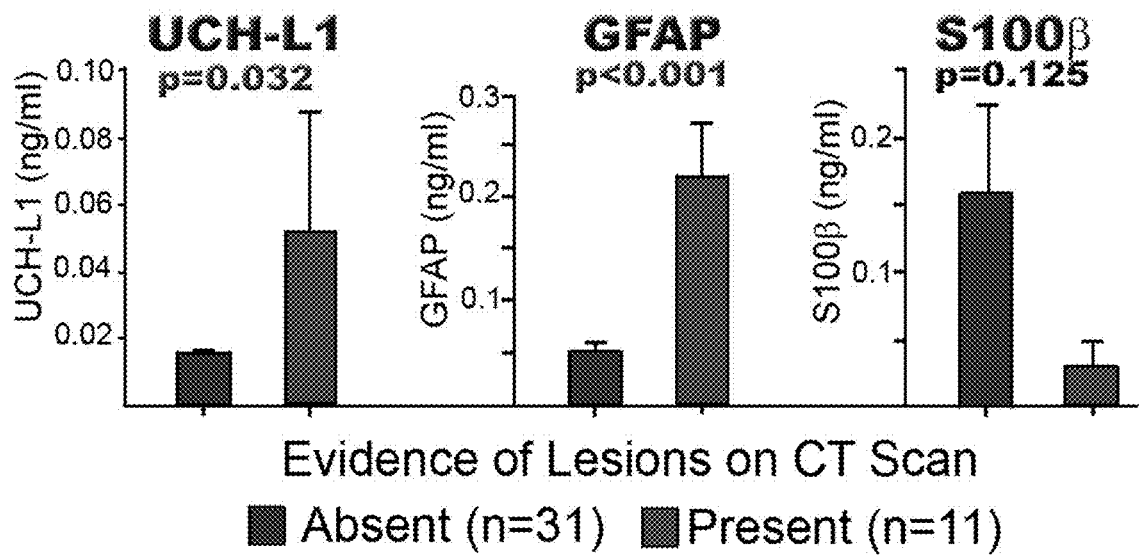
FIG. 19 are bar graphs showing the concentration of the same markers as depicted in FIG. 18 with respect to initial evidence upon hospital admission as to lesions in tomography scans.
Figure 20:
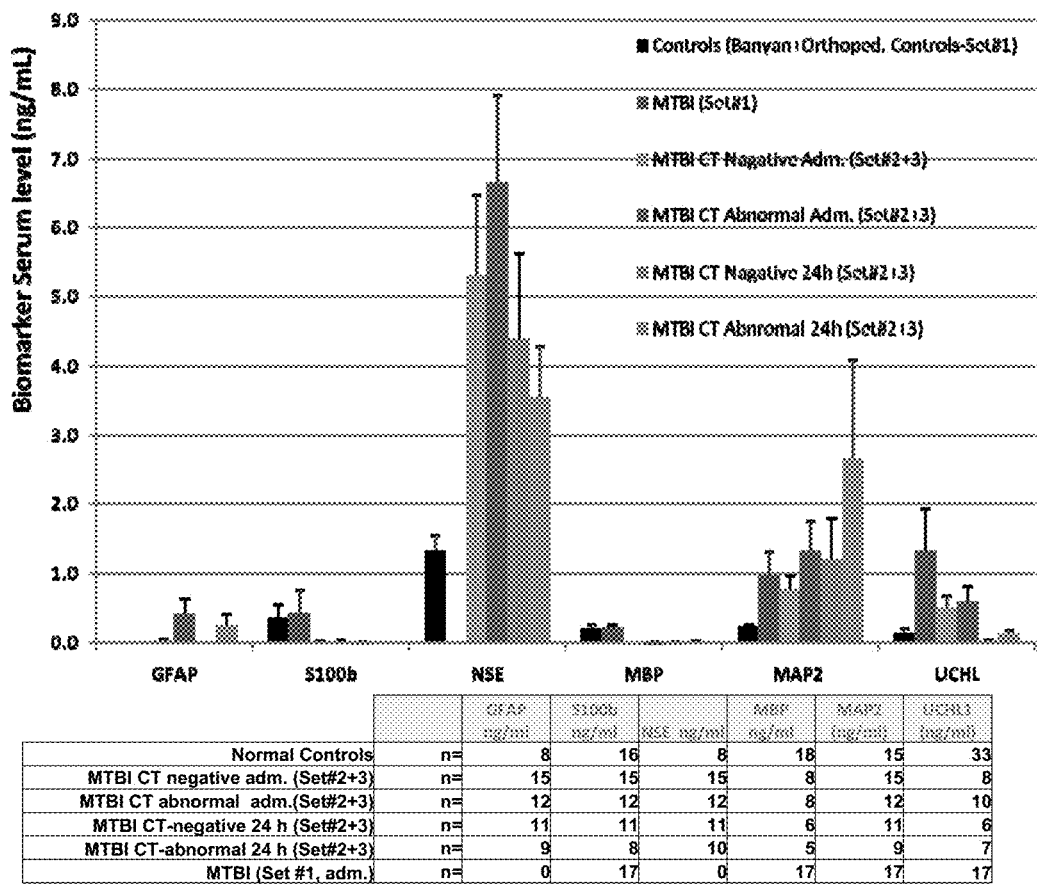
FIG. 20 represents biomarker levels in human subjects with varying types of brain injury.

FIG. 16 shows GFAP concentration for controls as well as individuals in the mild/moderate traumatic brain injury cohort as a function of CT scan results upon admission and 24 hours thereafter. Simultaneous assays were performed in the course of this study for UCH-L1 biomarker. The UCH-L1 concentration derived from the same samples as those used to determine GFAP is provided FIG. 17. The concentration of UCH-L1 and GFAP as well as a biomarker not selected for diagnosis of neurological condition, S100b, is provided as a function of injury magnitude between control, mild, and moderate traumatic brain injury as shown in FIG. 18. The simultaneous analyses of UCH-L1 and GFAP from these patients illustrates the synergistic effect of the inventive process in allowing an investigator to simultaneously diagnose traumatic brain injury as well as discern the level of traumatic brain injury between mild and moderate levels of severity. FIG. 19 shows the concentration of the same markers as depicted in FIG. 18 with respect to initial evidence upon hospital admission as to lesions in tomography scans illustrating the high confidence in predictive outcome of the inventive process. FIG. 20 shows that both NSE and MAP2 are elevated in subjects with MTBI in serum both at admission and at 24 hours of follow up. These data demonstrate a synergistic diagnostic effect of measuring multiple biomarkers such as GFAP, UCH-L1, NSE, and MAP2 in a subject.

Figure 21:
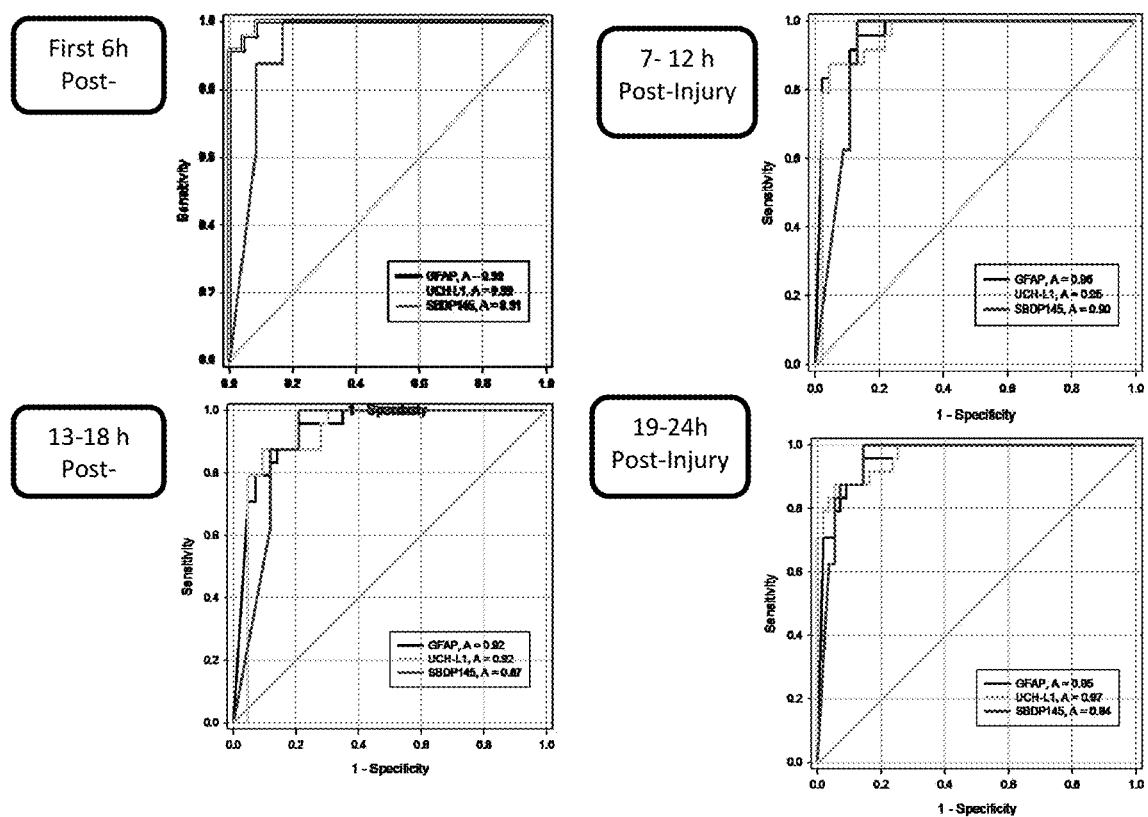
FIG. 21 are plots that represent ROC analysis of UCH-L1, GFAP and SBDP145 in human CSF (severe TBI vs. Control A) First 24 hours post-injury.

Through the simultaneous measurement of multiple biomarkers such as UCH-L1, GFAP, NSE, and MAP2, rapid and quantifiable determination as to the severity of the brain injury is obtained consistent with GSC scoring and CT scanning yet in a surprisingly more quantifiable, expeditious and economic process. Additionally, with a coupled assay for biomarkers indicative of neurological condition, the nature of the neurological abnormality is assessed and in this particular study suggestive of neuronal cell body damage. As with severe traumatic brain injury, gender variations are noted suggesting a role for hormonal anti-inflammatories as therapeutic candidates. A receiver operating characteristic (ROC) modeling of UCH-L1, GFAP and SBDP145 post TBI further supports the value of simultaneous measurement of these biomarkers, as shown in FIGS. 21, 22.

Figure 22:
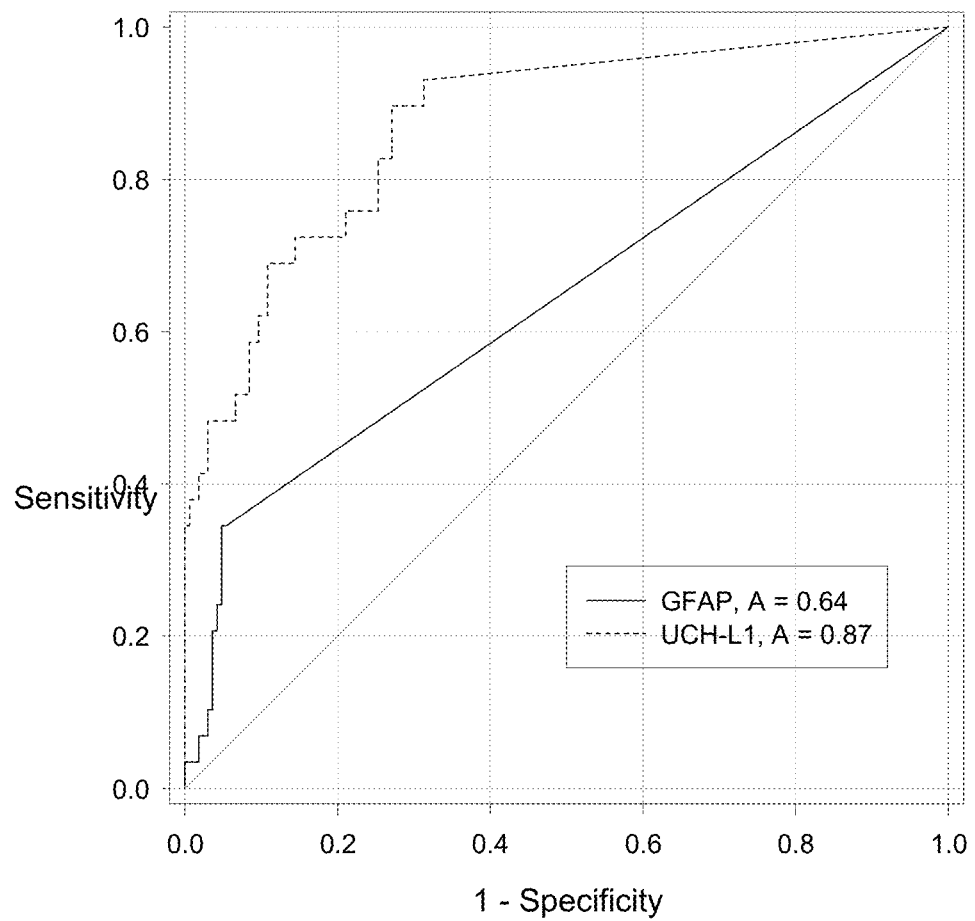
FIG. 22 is a plot that represent ROC analysis of UCH-L1 and GFAP in human CSF (mild TBI vs. normal Controls) a mean of 3h35' with a range 15'-14h35 post-injury.
Figure 23:
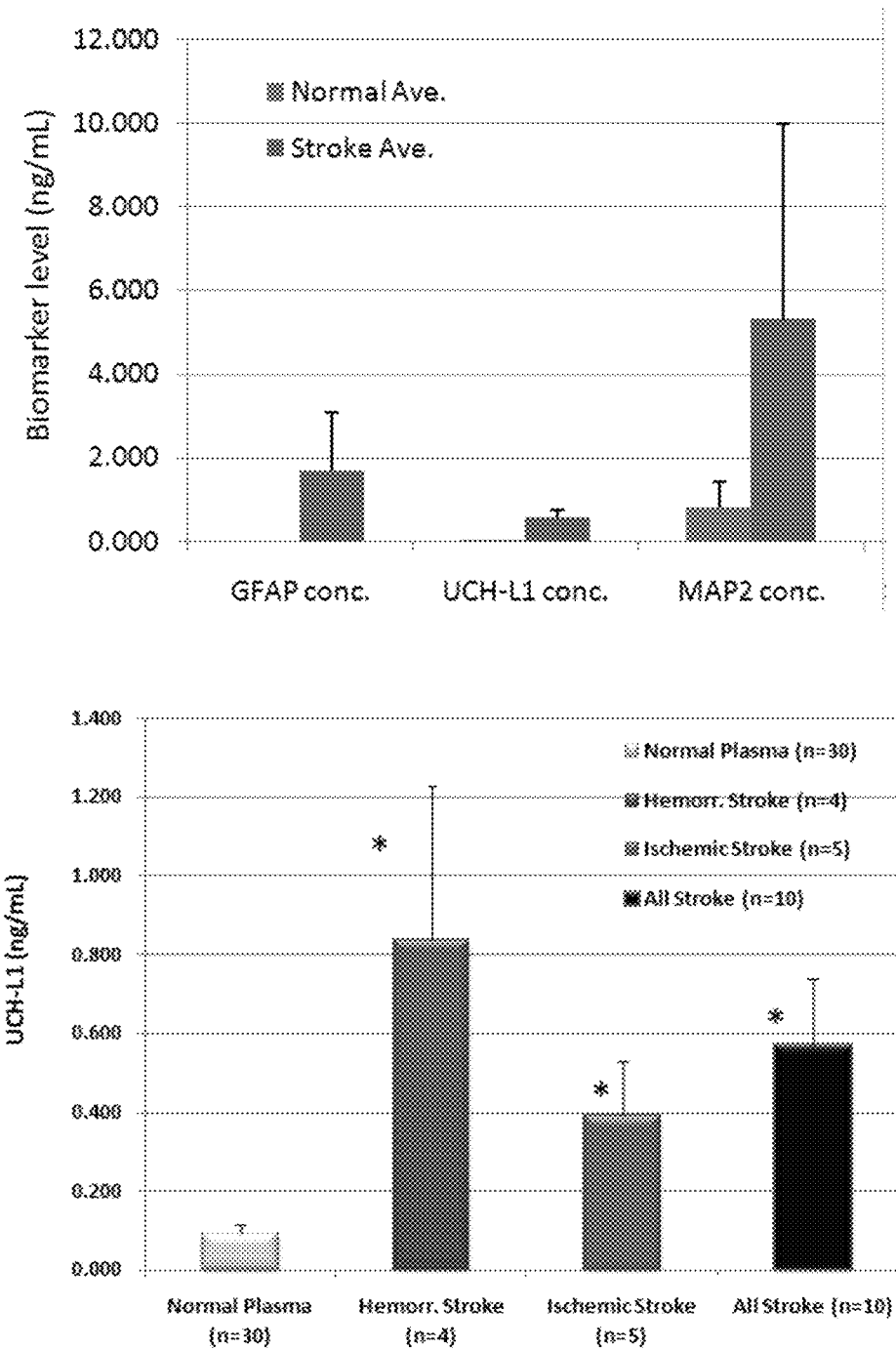
FIG. 23 are bar graphs of showing the elevation of brain injury biomarkers (GFAP, UCH-L1 and MAP2) in plasma from stroke patients.

In addition, FIG. 22 showed that several brain biomarkers (GFAP, UCH-L1 and MAP2) in stroke patients' plasma. Samples were collected with an average post-injury time 24.2 hr (range 18-30 h). Top panel shows GFAP, UCH-L1 and MAP2 levels in stroke (n=11) versus normal controls (n=30). Bottom panel further shows that UCH-L1 is elevated with both hemorrhagic and ischemic stroke populations when compared to normal control plasma.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for determining the neurological condition of a subject or cells from the subject, wherein the subject is known to have or is suspected of having a mild to moderate traumatic brain injury (TBI), wherein mild TBI is characterized as the subject having a Glasgow Coma Score (GCS) of 13-15 and moderate TBI is characterized as the subject having a GCS of 9-12, the process comprising:

measuring a sample obtained from the subject or cells from the subject at a first time for a quantity of a first biomarker, and a quantity of at least one additional neuroactive biomarker, wherein the first biomarker is glial fibrillary acidic protein (GFAP), and wherein the first time is within 12 hours of the TBI or the suspected TBI;

comparing the quantity of said first biomarker and the quantity of said at least one additional neuroactive biomarker to normal levels of said first biomarker and said at least one additional neuroactive biomarker;

predicting a presence of an intracranial lesion in the subject based on the quantity of said first biomarker and said additional neuroactive biomarker relative to the normal levels of said first biomarker and said at least one additional neuroactive biomarker, wherein a presence of an intracranial lesion is predicted if said first biomarker and/or said at least one additional neuroactive biomarker are elevated relative to the normal levels of said first biomarker and said at least one additional neuroactive biomarker;

wherein an absence of an intracranial lesion is predicted if said first biomarker and said at least one additional neuroactive biomarker are not elevated relative to the normal levels of said first biomarker and said at least one additional neuroactive biomarker; and performing a head CT on the subject when the presence of an intracranial lesion is predicted or declining a head CT on the subject when the absence of an intracranial lesion is predicted.

2. The process of claim 1, wherein the sample is cerebrospinal fluid, plasma, or blood serum.

3. The process of claim 1, wherein the subject has been exposed to a drug candidate or an environmental contaminant and the sample is a culture of cells from the subject.

4. The process of claim 1, wherein said at least one additional neuroactive biomarker is selected from the group of ubiquitin carboxyl-terminal hydrolase L1 (UCH-L1), neuron specific enolase (NSE), spectrin breakdown products 150 (SBDP150), SBDP145, SBDP120, 5100 calcium binding protein B (S100b), microtubule-associated protein 2 (MAP2), MAP1, MAP3, MAP4, MAPS, myelin basic protein (MBP), Tau, Neurofilament protein (NF), Cannabinoid Receptor CB, CAM, Synaptic protein, collapsin response mediator proteins (CRMP), inducible nitric oxide synthase (iNOS), Neuronal Nuclei protein (NeuN), 2',3'-cyclic nucleotide-3'-phosphohydrolase (CNPase), Neuroserpin, alpha-internexin, microtubule-associated protein 1 light chain 3 (LC3), Neurofascin, the glutamate transporters (EAAT), Nestin, Cortin-1, and BIII-Tubulin.

5. The process of claim 1, further comprising measuring a second quantity of said first biomarker and a second quantity of said at least one additional neuroactive biomarker at a second time to yield a kinetic profile for said first biomarker and said at least one additional neuroactive biomarker, wherein the second time is within 12 hours of the TBI or the suspected TBI.

6. The process of claim 1, further comprising comparing the quantity of said first biomarker and the quantity of said at least one additional neuroactive biomarker between normal levels in the subject to other individuals of the same gender as the subject.

7. The process of claim 1, wherein said at least one additional neuroactive biomarker is UCH-L1.

8. The process of claim 1, further comprising determining if the subject or cells from the subject has been exposed to some degree of traumatic brain injury ranging from mild to moderate.

9. The process of claim 8, wherein said at least one additional neuroreactive biomarker is UCH-L1, and the process further comprises identifying the magnitude of TBI based on the quantity of UCH-L1 and the quantity of GFAP.

10. The process of claim 8, wherein mild traumatic brain injury and moderate traumatic brain injury have detection cutoffs for UCH-L1 and GFAP in serum of 0.39 ng/ml and 1.4 ng/ml, respectively.

11. The process of claim 1, wherein the at least one additional neuroactive biomarker is S100b.

12. The process of claim 1, wherein the at least one additional neuroactive biomarker is selected from the group of SBDP150, SBDP150i, SBDP145, or SBDP120.

13. The process of claim 1, wherein the at least one additional neuroactive biomarker is NSE.

14. The process of claim 1, wherein the at least one additional neuroactive biomarker is selected from the group of MAP2, MAP1, MAP3, MAP4, or MAPS.

15. A method of assaying a biomarker combination after a traumatic brain injury (TBI), comprising:

obtaining a blood or cerebral spinal fluid (CSF) sample collected from a subject having the TBI within 12 hours after occurrence of the TBI; and measuring levels of ubiquitin carboxyl-terminal hydrolase L1 (UCH-L1) and glial fibrillary acidic protein (GFAP) by assaying the blood or CSF sample.

16. The method of claim 15, wherein the blood or CSF sample is a blood sample.

17. The method of claim 16, wherein the blood sample is collected from the subject within 2 hours after the occurrence of the TBI.

18. A method of performing a head CT scan, comprising:

measuring levels of UCH-L1 and GFAP by performing the method of claim 16; and performing the head CT scan on the subject when the levels of UCH-L1 and/or GFAP exceed predetermined cutoff values.

19. A method of refraining from performing a head CT scan on a subject having a TBI, comprising:

measuring levels of UCH-L1 and GFAP by performing the method of claim 16; and refraining from performing the head CT scan on the subject when the levels of UCH-L1 and GFAP do not exceed predetermined cutoff values.

* * * * *